United States Patent
Feinberg

(10) Patent No.: US 8,691,572 B2
(45) Date of Patent: Apr. 8, 2014

(54) DIAGNOSING, MONITORING AND TREATING INFLAMMATION

(75) Inventor: Mark W. Feinberg, Newton, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 1172 days.

(21) Appl. No.: 12/464,037

(22) Filed: May 11, 2009

(65) Prior Publication Data
US 2010/0016938 A1     Jan. 21, 2010

Related U.S. Application Data

(63) Continuation-in-part of application No. PCT/US2007/023680, filed on Nov. 9, 2007.

(60) Provisional application No. 60/858,430, filed on Nov. 10, 2006, provisional application No. 61/117,228, filed on Nov. 23, 2008.

(51) Int. Cl.
*C12N 5/00* (2006.01)
*C12N 5/02* (2006.01)
*C12Q 1/68* (2006.01)
*C12N 5/071* (2010.01)

(52) U.S. Cl.
USPC .......................... 435/375; 435/372.3; 435/6.1

(58) Field of Classification Search
None
See application file for complete search history.

(56) References Cited

U.S. PATENT DOCUMENTS

2005/0249770 A1    11/2005  Hunter

OTHER PUBLICATIONS

Spittau et al., 2010, J. Neur. Res. vol. 88: 2017-25.*
Johnsen et al., 2002, Oncogene, vol. 21: 5783-90.*
International Search Report (PCT/ISA/2010) issued in PCT/US2007/023680, Dec. 9, 2008, The Brigham and Women's Hospital, Inc.
Cao et al., The kruppel-like factor 10 (KLF10) induces a T Regulatory phenotype and suppresses inflammatory markers. Circulation. Oct. 31, 2006, vol. 114, No. 18, Suppl. S. pp. 120-121, see entire document.
Sugimoto et al., Foxp3-dependent and -independent molecules specific for CD25+CD4+natural regulatory T cells revealed by DNA microarray analysis. Int Immunol. Aug. 2006, vol. 18, No. 8, pp. 1197-1209. Epub Jun. 13, 2006, see, in particular, p. 1200, right column.
Venuprasad et al. The E3 ubiquitin ligase Itch regulates expression of transcription factor Foxp3 and airway inflammation by enhancing the function of transcription factor TIEGI. Nat Immunol. Mar. 2008, vol. 9, No. 3 pp. 245-253, see entire document.

* cited by examiner

*Primary Examiner* — Amy Juedes
(74) *Attorney, Agent, or Firm* — David S. Resnick; Nixon Peabody LLP

(57) ABSTRACT

The present invention provides methods and compositions for treating chronic inflammatory disease in a subject and associated pharmaceutical compositions, medical devices and systems.

1 Claim, 29 Drawing Sheets

Foxp3 PROMOTER:
(-165bp)                    KLF              (-127bp)
HUMAN: AAAACTATGAG|AACCCCCCCCCA|CCCCGTGATTATCAGCG
  COW: AAAACTATGAG|AACCCCCCCCCA|CCCCGTGATTATC
  CAT: AAAACTATGAG|AACCCCCCCCCA|CCCCGTGATTATC
MOUSE: AAAACTACAAG|AACCCCCCCCCC|ACCCTGCAATTATC
  RAT: AAAACTACGAG|AACCCCCCCACC|CTGCGATTATC WT: CCCCCCCCACCCC
MUT: CC<u>TTTT</u>C<u>G</u>AA<u>TTC</u>

SEQUENCE LISTING

```
<160> NUMBER OF SEQ ID NOS: 39

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cccatcccca ggagtcttg                                                  19

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 2
accatgacta ggggcactgt a                                                   21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttctctccag caagcttcgg a                                                   21

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcactctgct cagctttgtc cc                                                  22

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggacctaaac aacgtgttgg a                                                   21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctccgggtag tagaaggcag                                                     20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgatggtgct tggtgagttg                                                     20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
```

```
ttgcacatct gaaaccacag                                              20
```

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
ttccaaactg gcgattcaca a                                            21
```

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
attaactggc agagtggcag gtaa                                         24
```

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
cctgttgtgg tccaagttca ac                                           22
```

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
cacaaacatc ctgtaatggc ttgt                                         24
```

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
gccatgggtt agagaggcag                                              20
```

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

```
ttggagactc ctcacgcatg t                                            21
```

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 15
gtgctccttg tcaacagcg                                         19

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 16
ggggagtttc aggttcctgt a                                      21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 17
gaactggcaa aaggatggtg a                                      21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 18
tgtgggttgt tgacctcaaa c                                      21

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 19
atcctgtcca aactaaggct cg                                     22

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 20
acctctttag catagtagtc cgc                                    23

-continued

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gaaatcgtgc gtgacatcaa ag                                              22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tgtagtttca tggatgccac ag                                              22

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggtctcaacc cccagctagt                                                 20

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gccgatgatc tctctcaagt gat                                             23

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tttaactccc ttggcgcaaa a                                               21

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctttccctcc gcattgacac                                                 20

<210> SEQ ID NO 27
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggacgctgct gagtggaaga g                                              21

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aaggcaggga gcggagac                                                  18

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gtggtgaggg gaagaaatc                                                 19

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cgtggaagcc gcagacctc                                                 19

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aaactatgag aaccttttcg aattccgtga ttatcagcgc                          40

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcgctgataa tcacggaatt cgaaaaggtt ctcatagtt                           39

<210> SEQ ID NO 33
<211> LENGTH: 40
<212> TYPE: DNA
<213> ORGANISM: Homo sapiens
```

```
<400> SEQUENCE: 33
aaaactatga gaaccccccc ccaccccgtg attatcagcg                40

<210> SEQ ID NO 34
<211> LENGTH: 36
<212> TYPE: DNA
<213> ORGANISM: Bos sp.

<400> SEQUENCE: 34
aaaactatga gaaccccccc ccaccccgtg attatc                   36

<210> SEQ ID NO 35
<211> LENGTH: 36
<212> TYPE: DNA
<213> ORGANISM: Felis sp.

<400> SEQUENCE: 35
aaaactatga gaaccccccc ccaccccgtg attatc                   36

<210> SEQ ID NO 36
<211> LENGTH: 37
<212> TYPE: DNA
<213> ORGANISM: Mus sp.

<400> SEQUENCE: 36
aaaactacaa gaaccccccc cccaccctgc aattatc                  37

<210> SEQ ID NO 37
<211> LENGTH: 34
<212> TYPE: DNA
<213> ORGANISM: Rattus sp.

<400> SEQUENCE: 37
aaaactacga gaaccccccc accctgcgat tatc                     34

<210> SEQ ID NO 38
<211> LENGTH: 13
<212> TYPE: DNA
<213> ORGANISM: Unknown
<220> FEATURE:
<223> OTHER INFORMATION: Description of Unknown: Unknown WT
      oligonucleotide

<400> SEQUENCE: 38 cccccccac ccc                                             13

<210> SEQ ID NO 39
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ccttttcgaa ttc                                            13
```

DIAGNOSING, MONITORING AND TREATING INFLAMMATION

CROSS-REFERENCE TO RELATED APPLICATIONS/PATENTS & INCORPORATION BY REFERENCE

This application is a continuation-in-part of PCT International Application Serial No. PCT/US2007/023680, filed Nov. 9, 2007, designating the United States and published in English on May 22, 2008 as publication WO 2008/060485 A3, which claims priority to U.S. provisional application Ser. No. 60/858,430, filed Nov. 10, 2006. This application also claims priority to U.S. provisional application Ser. No. 61/117,228, filed Nov. 23, 2008. The entire contents of the aforementioned patent applications are incorporated herein by this reference.

Any and all references cited in the text of this patent application, including any U.S. or foreign patents or published patent applications, International patent applications, as well as, any non-patent literature references, including any manufacturer's instructions, are hereby expressly incorporated herein by reference.

GOVERNMENT SUPPORT

This invention was made with government support under Grant Number HL080174 awarded by the National Institutes of Health, an agency of the U.S. Department of Health and Human Services. The government has certain rights in the invention.

BACKGROUND

1. Field of the Invention

The present invention relates to the field of treating chronic inflammatory diseases.

2. Background of the Invention

T regulatory cells, or T reg cells, are a subclass of T cells, capable of inhibiting Th1- and Th2-driven inflammatory responses that contribute to the development of autoimmune diseases, such as, type I diabetes, multiple sclerosis, inflammatory bowel disease, and atherosclerosis, among others. Of particular interest is the identification of novel molecular mechanisms underlying the development and suppression function of T regs as a means for establishing new strategies for treating autoimmune diseases.

With respect to atherosclerosis, atherogenesis is the developmental process that results in the formation of atheromatous plaques, which may lead to atherosclerosis. T cell activation plays an important role in atherogenesis (e.g., by macrophage activation/recruitment; SMC proliferation; and collagen formation). For example, it has been shown that injection of Tr1 T regulatory cells—a subset of T regs that have been previously identified, along with natural regulatory CD4+CD25+ cells and Th3 cells—was able to decrease atheroma size in ApoE−/−mice (Mallat Z. et al., 2003). In addition, injection of CD4+CD25+ T regulatory cells was able to reduce lesion size in mouse models of atherosclerosis. The same study also showed that a depletion of T regulatory cells accelerated atherosclerosis in mice (Ait-Oufella et al., 2006). Thus studies have shown an important role for T reg cells in inhibiting the progression of atherosclerosis in mice.

It has been previously shown that TGF-$\beta$1 (transforming growth factor $\beta$1) may play a role in regulating the activity of T reg cells. TGF-$\beta$1 is a pleiotropic growth factor important in cell growth, differentiation, and activation in a number of immune and non-immune cell types (Feinberg and Jain, 2005; Li and Flavell, 2008; Shi et al., 1999). TGF-$\beta$1 is involved in the maintenance of self-tolerance and homeostasis of several T cell effectors including T regulatory cells (Fantini et al., 2004; Li et al., 2006; Wan and Flavell, 2005). Indeed, disruption of TGF-$\beta$1 or its receptors in T cells induces a severe lymphoproliferative response and autoimmunity (Marie et al., 2006; Shull et al., 1992). Thus, tight control of TGF-$\beta$1 and its downstream signaling pathways may allow for fine-tuning of the immune response by modulating T regulatory cell development or function. With particular regard to atherosclerosis, the effect of T regulatory cells in limiting atherosclerosis has been shown to be dependent in part on TGF-$\beta$ signaling. TGF-$\beta$ has potent immunosuppressive effects on multiple cell types, including effects on T cell activation, SMC proliferation, collagen formation, endothelial proliferation, and macrophage activation.

Additionally, with regard to CD4+CD25+ T reg cells, TGF-$\beta$1 signaling is believed to be required for the differentiation of CD4+CD5− T reg cells to CD4+CD5+ T reg cells. TGF-$\beta$ is also required for peripheral maintenance of CD4+CD25+ cells and their suppression function, but not for their thymic development (Marie et al., 2005). The suppression function of CD4+CD25+ cells includes inhibition of the inflammation response, e.g., due to the immune response to intracellular pathogens. Because inflammation is also associated with pathologies such as atherosclerosis, type I diabetes, and multiple sclerosis, TGF-$\beta$1 signaling may inhibit atherosclerosis by conferring T regulatory function and control of inflammation.

An additional possible regulator of T reg cells are the Kruppel-like family of proteins, or KLFs, which a family of related zinc-finger transcription factors that have roles in various aspects of cellular growth, development and differentiation, particularly in the hematopoietic system. Several KLFs with these properties have been identified, including KLFs 1-4. KLF1, or EKLF has been shown to be essential for erythropoiesis. KLF2, or LKLF (KLF2) plays a role in T-lymphocyte development. KLF3, or BKLF, has been implicated in the of myeloproliferative disorder. KLF4 or GKLF, is involved in epithelial development, including differentiation of gut, skin, monocyte. Because of the importance of KLFs in different hematopoietic lineages, Kruppel-like zinc-finger protein may regulate the differentiation or function of T reg cells.

Due to the wide prevalence of autoimmune diseases, including type I diabetes, multiple sclerosis, inflammatory bowel disease, and atherosclerosis, among others, as well as the limited treatment options that are available, there remains a need for new strategies for developing and obtaining useful therapeutics for combating these disorders.

SUMMARY OF THE INVENTION

The purpose and advantages of the present invention will be set forth in and become apparent from the description that follows. Additional advantages of the invention will be realized and attained by the methods and systems particularly pointed out in the written description and claims hereof, as well as from the appended drawings.

It has been discovered that KLF10 is expressed in T regulatory cells and modulates T regulatory function. Without being bound to a particular theory, KLF10 has at least two activities that modulate T regulatory function, i.e., inducing Foxp3 and negatively regulating NFAT. Applicants' discovery, accordingly, provides for uses of KLF10 as described herein.

To achieve these and other advantages and in accordance with the purpose of the invention, as embodied herein, the invention includes, among other things, a method of detecting, from a patient's blood sample, expression of KLF10 as a relative marker for inflammatory disease states such as coronary artery disease, among others. Such assays to identify KLF10 may include a chip, plate, liquid, bead, or membrane array and the like. In addition, if desired the KLF10 promoter (5'UTR) may be used as a screen to identify molecules or compounds that may be important for modulating T regulatory cell function or cell number and, as a consequence, the development of inflammatory disease states, autoimmune disease, multiple sclerosis, and cancer, among others. Finally, KLF10 itself may be used to generate or promote increased number or function of CD4+CD25+ T regulatory cells which may be used in a wide variety of applications in which suppressing inflammation is important for limiting disease progression. Various systems can be used to facilitate localized delivery of compounds to treat inflammation in accordance with the invention.

In one aspect, the invention provides methods for treating a chronic inflammatory disease in a subject in need thereof, comprising administering to the subject a therapeutically effective amount of a KLF10 polypeptide or fragment thereof, wherein the KLF10 polypeptide or fragment thereof induces a T regulatory phenotype.

In one embodiment, the KLF10 protein or fragment thereof is systemically administered. In another embodiment, the KLF10 polypeptide or fragment thereof is administered locally at a site of inflammation In one embodiment, the KLF10 polypeptide or fragment thereof further comprises an intracellular cargo delivery ligand.

In one embodiment, the KLF10 polypeptide or fragment thereof is administered by gene therapy. In a further embodiment, administration by gene therapy comprises delivery of an expression vector capable of expressing the KLF10 polypeptide or fragment thereof.

In one embodiment, the invention provides methods for treating a chronic inflammatory disease in a subject in need thereof, according to one or more of the preceding aspects and embodiments, and further comprising contacting a CD4+/CD25− cell with the KLF10 or fragment thereof, whereby the step of contacting results in a conversion of the CD4+/CD25− cell to a CD4+/CD25+ cell.

In one embodiment, the inflammatory disease is a coronary artery disease. In another embodiment, the inflammatory disease is atherosclerosis. In another embodiment, the inflammatory disease is type 1 diabetes. In another embodiment, the inflammatory disease is multiple sclerosis.

In one embodiment, the KLF10 polypeptide or fragment thereof is administered on an implantable stent. In another embodiment, the KLF10 polypeptide or fragment thereof is administered by myocardium injection.

In a specific embodiment, the KLF10 polypeptide or fragment thereof is administered by gene therapy. The administration by gene therapy comprises delivery of an expression vector capable of expressing the KLF10 polypeptide or fragment thereof and the expression vector is administered by myocardium injection.

In a specific embodiment, the KLF10 polypeptide or fragment thereof is administered by gene therapy. The administration by gene therapy comprises delivery of an expression vector capable of expressing the KLF10 polypeptide or fragment thereof and the expression vector is administered on an implantable stent.

In another aspect, the invention provides methods for identifying a candidate compound that may modulate a KLF10-induced T regulatory phenotype. The methods comprise the steps of contacting a KLF10-sensitive reporter gene with the KLF10 polypeptide both in the presence and the absence of the candidate compound; detecting the expression level of the KLF10-sensitive reporter gene; and comparing the expression level of the KLF10-sensitive reporter gene in the presence and absence of the candidate compound. A modulated level of expression of the KLF10-sensitive reporter gene in the presence of the candidate compound is indicative of a compound that may modulate a KLF10-induced T regulatory phenotype.

In one embodiment, the methods further comprise testing the candidate compound in an animal model to determine whether the candidate compound modulates a KLF10-induced T regulatory phenotype.

In yet another aspect, the invention provides methods for identifying a candidate compound that induces the T regulatory phenotype in CD4+/CD25− cells. The methods comprise the steps of contacting a CD4+/CD25− cell comprising a reporter gene under the control of a KLF10 promoter with a candidate compound; detecting the expression level of the reporter gene, wherein upregulation of the reporter gene is indicative of a compound that induces the T regulatory phenotype.

In one embodiment, the methods further comprise testing the candidate compound in an animal model to determine whether the candidate compound modulates a KLF10-induced T regulatory phenotype.

In still another aspect, the invention provides pharmaceutical compositions comprising a therapeutically effective dose of a KLF10 polypeptide or fragment thereof and a pharmaceutically acceptable excipient.

In one aspect, the invention provides kits comprising a therapeutically effective dose of a KLF10 polypeptide or fragment thereof and instructions for use in treating a chronic inflammatory disease.

In one embodiment, the chronic inflammatory disease is atherosclerosis, type 1 diabetes, multiple sclerosis, an autoimmune disease, an inflammatory cardiac disease, or cancer.

In one aspect, the invention provides kits comprising a therapeutically effective dose of an expression vector encoding a KLF10 polypeptide or fragment thereof and instructions for use in treating a chronic inflammatory disease.

In one embodiment, the chronic inflammatory disease is atherosclerosis, type 1 diabetes, multiple sclerosis, an autoimmune disease, an inflammatory cardiac disease, or cancer.

In another aspect, the invention provides stents comprising a plurality of interconnected struts, wherein at least one of the struts includes a beneficial agent including a therapeutically effective amount of a KLF10 polypeptide or fragment thereof disposed thereon.

In one embodiment, the beneficial agent is disposed in a polymeric medium formed on the strut. In another embodiment, the beneficial agent is disposed in a depression formed in the strut. In yet another embodiment, the stent is formed substantially of a polymeric material.

In yet another aspect, the invention provides a system for treating a patient, comprising a stent delivery catheter; and a stent disposed on the stent delivery catheter. The stent comprises a plurality of interconnected struts, wherein at least one of the struts includes a beneficial agent including a therapeutically effective amount of a KLF10 polypeptide or fragment thereof disposed thereon.

In one embodiment, the stent delivery catheter is an over the wire catheter. In another embodiment, the stent delivery catheter is a rapid exchange catheter.

In another embodiment the stent delivery catheter includes a retractable sheath that exposes the stent when the sheath is retracted. In a specific embodiment, the stent is a self-expanding stent.

It is to be understood that both the foregoing general summary and the following detailed description are exemplary and are intended to provide further explanation of the invention claimed.

BRIEF DESCRIPTION OF THE DRAWINGS

The following Detailed Description, given by way of example, but not intended to limit the invention to specific embodiments aspects described, may be understood in conjunction with the accompanying drawings, which incorporated herein by reference. Various features and aspects of the present invention will now be described by way of non-limiting examples and with reference to the accompanying drawings, in which.

DETAILED DESCRIPTION OF THE INVENTION

Figure 1A:
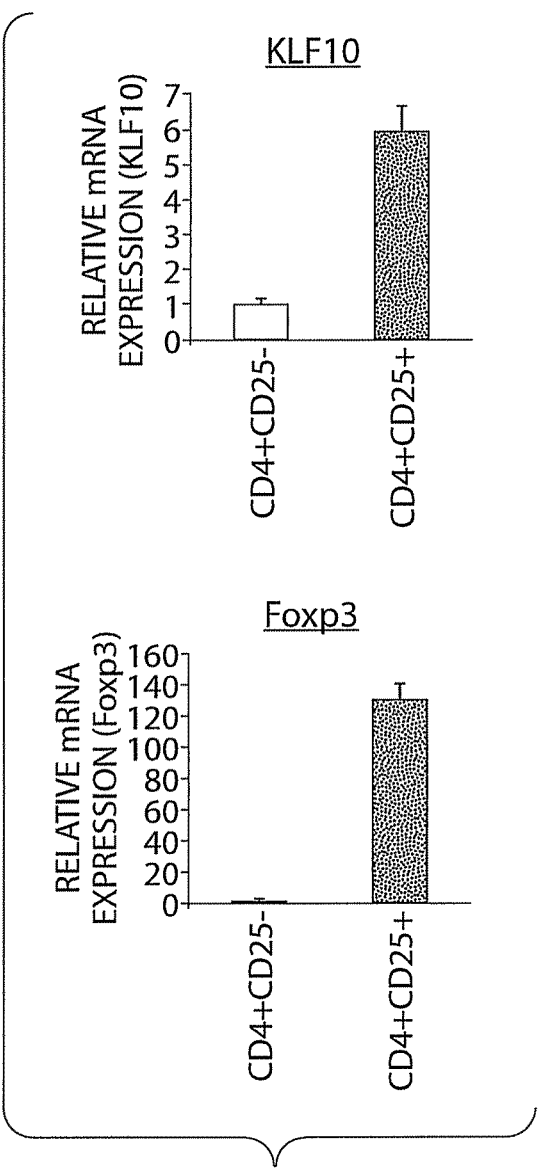
FIG. 1 depicts KLF10 expression in $CD4^+CD25^+$ T regulatory cells. (A) Real-time qPCR analyses of KLF10 mRNA in $CD4^+CD25^-$ and $CD4^+CD25^+$ T cells isolated from spleens of mice demonstrate that KLF10 (left) is highly expressed in $CD4^+CD25^+$ T regulatory cells. Expression of the T regulatory marker Foxp3 (right) was used as a positive control. (B) qPCR analyses show that other KLFs (KLF2, KLF4, and KLF5) were either not changed or decreased. (C) $CD4^+CD25^-$ T cells were treated for TGF-$\beta$1 at the indicated time points, and total RNA was harvested for qPCR analyses. KLF10 (left) and Foxp3 (right) mRNAs are rapidly induced by TGF-$\beta$1 at 1 hr and 6 hrs, followed by reduced expression at 24 hrs. (D and E) TGF-$\beta$1 responsiveness of KLF10 was also assessed using the Jurkat T cell line. Total RNA was subjected to Northern analysis (10 μg/lane) after cells were treated with TGF-$\beta$1 at the indicated time points (D) or in a dose-dependent manner (E). KLF10 mRNA was induced in a time- and dose-dependent manner in Jurkat cells. (F) Depicts the expression of KLF10 mRNA in response to stimulation by α-CD3; (G) Depicts the effect of ApoE deficiency on the expression of KLF10 mRNA.

Unless defined otherwise, all technical and scientific terms used herein have the meaning commonly understood by a person skilled in the art to which this invention belongs. The following references, the entire disclosures of which are incorporated herein by reference, provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms may have the meanings ascribed to them below, unless specified otherwise. However, it should be understood that other meanings that are know or understood by those having ordinary skill in the art are also possible, and within the scope of the present invention.

As used herein, the expression "therapeutically effective amount" of KLF10 or a fragment thereof is the amount of KLF10 or KLF10 fragment that is sufficient to generate or promote, inter alia, a T regulatory phenotype. The T regulatory phenotype is characterized by an increased number and/or or function of CD4+/CD25+ T regulatory cells.

As used herein, the expression "intracellular cargo delivery ligand" is meant to refer to any peptide or ligand which can be attached to a polypeptide of interest, e.g. the KLF10 polypeptide, in order to facilitate entry of the polypeptide of interest into a cell, e.g. a CD4+/CD25− cell of the invention. Such ligands generally may include peptides, e.g., the Tat-derived peptide. Methods for utilizing such peptides are well known in the art.

It will be appreciated that the KLF10 polypeptide of the invention is not limited to the human sequence, GenBank Accession No. NM_001032282, but can include other KLF10 polypeptides, such as, other human sequences (e.g. natural variants), mouse (GenBank Accession No. NM_013692), monkey, rabbit, cow, etc., and especially, can include those variants which are optimized based on a human KLF10 or which are generated by any recombinant means known in the art, e.g. site-directed mutagenesis. With reference to the human KLF10 polypeptide sequence of GenBank No. NM_001032282 (or translated version thereof), the present invention contemplates functional fragments thereof, e.g. the protein-binding domain or the DNA-binding domain, or variants of such fragments or the whole or substantially the whole polypeptide which preferably have about 80% sequence identity, more preferably about 85% sequence identity, still more preferably about 90% sequences identity, even more preferably about 95% or even 99% sequence identity with the human reference polypeptide sequence above.

As used herein, the term "KLF10-sensitive reporter" refers to a reporter gene whose transcription is controlled or modulated by KLF10.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Other definitions appear in context throughout this disclosure.

Reference will now be made in detail to various embodiments of the invention, an example of which is illustrated in the accompanying drawings. The method and corresponding steps of the invention will be described in conjunction with the detailed description of the system.

The devices and methods presented herein may be used for diagnosing, monitoring, and/or treating inflammation including the treatment of disorders in which the limitation of inflammation is beneficial.

As embodied herein, the invention provides a platform for identifying and screening compounds that are advantageous for inducing or reducing T regulatory cell function with many applications in diseased patients. This accordingly permits for a more stringent approach for identifying such compounds than exists currently since only one other transcription factor to date (Foxp3) has been found to regulate T regulatory cells. Since it has been discovered herein by both gain and loss of function studies that KLF10 directly regulates Foxp3, KLF10 is believed to be more upstream and to have more pronounced effects. Thus, in accordance with an embodiment of the invention, KLF10 may be used as an alternative to Foxp3 as a regulator of T regulatory cell function and differentiation. If desired, local administration of KLF10, peptides derived from KLF10, or cells overexpressing KLF10, can ameliorate a host of inflammatory conditions. This is particularly attractive as systemic administration of anti-inflammatory agents (ie. prednisone or steroids) can cause significant unwanted side effects and can even be detrimental (for example, decreased bone density, GI side effects, weight gain, mood effects, among others).

Also, emerging evidence suggests use of NSAIDS or Cox-2 inhibitors will increase the risk of heart attacks. Thus, local application of compounds of KLF10 itself or identified by regulating a KLF10 reporter system will avoid any untoward side effects of systemic administration of anti-inflammatory drugs.

Herein is disclosed a member of the Kruppel-like family of transcription factors (KLF10) that is TGF-β responsive and a novel regulator of T regulatory cells.

A physician can apply KLF10 to reduce inflammation in a variety of conditions as described above. In addition, biotech or pharmaceutical companies can use the KLF10 reporter to screen for compounds or molecules important in affecting T regulatory cell numbers or function. Thus, KLF10 may be used as 1) an end-product to reduce inflammation or for diagnosing or monitoring non-invasively relative inflammation in peripheral blood of patients. Such assays to identify KLF10 may include a chip, plate, liquid, bead, or membrane array etc. or 2) as a technique for identifying compounds in high-throughput assays using KLF10 as a reporter.

Accordingly, embodiments of the invention provide a tool for identifying compounds that will promote or reduce T regulatory cell number or function. T regulatory cells have been shown to limit the development or progression of a wide variety of diseases including diabetes, atherosclerosis, multiple sclerosis, inflammatory bowel disease and certain types of cancer, among others. Such compounds that regulate the KLF10 promoter may be identified, for example, using a high-throughput reporter assay in immature CD4+CD25− cells. Induction of KLF10 reporter by a compound would indicate that it may be capable of promoting cell differentiation to CD4+CD25+ T regulatory cells since overexpressing or activating KLF10 itself is capable of promoting T regulatory cell phenotype and function. Finally, KLF10 itself through gene delivery techniques can help to limit inflammatory responses in a number of disease states as stated above. For example, administration of KLF10, peptides derived from KLF10, or cells overexpressing KLF10, may ameliorate rheumatoid arthritis after injection into bone joints or may ameliorate inflammatory effects in the setting of acute coronary syndromes when delivered by intracoronary injection.

EXAMPLES

Example 1

KLF10 is a Regulator of T reg Differentiation, Suppression Function and CD4+CD25− T Cell Activation Introduction Immunological tolerance is maintained by a subset of T cells known as CD4$^+$CD25$^+$ regulatory T cells (T regs) that express Foxp3 and possess powerful immunosuppressive functions. T regs constitute ~5-10% of peripheral CD4$^+$ T cells in healthy animals and humans; however, reduced numbers or function of T regs have been associated with the development of autoimmune diseases such as type I diabetes, multiple sclerosis, inflammatory bowel disease, or atherosclerosis, among others (Bluestone and Tang, 2005; Fontenot and Rudensky, 2005; Piccirillo and Shevach, 2004; Sakaguchi, 2005; Ziegler, 2006). Indeed, mutation of Foxp3 is associated with a reduction of T regs in mice and leads to a fatal X-linked autoimmune disorder known as scurfy, whereas in humans it is associated with the development of immune dysregulation, polyendocrinopathy, enteropathy, X-linked syndrome (IPEX) (Bennett et al., 2001; Chatila et al., 2000). Recent studies provide evidence that CD4$^+$CD25$^+$ T regs may arise in the periphery from CD4$^+$CD25$^-$ T cells in response to a variety of stimuli both in vitro and in vivo, an effect, in part, dependent upon induced Foxp3 expression (Bettelli et al., 2006; Carrier et al., 2007; Chen et al., 2003; Davidson et al., 2007; Fantini et al., 2004; Fu et al., 2004; Kretschmer et al., 2005; Wan and Flavell, 2005; Zheng et al., 2004). Thus, identification of novel molecular mechanisms underlying the development and suppression function of T regs in the periphery is of considerable scientific and therapeutic interest.

Transforming growth factor (TGF)-β1 is a pleiotropic growth factor important in cell growth, differentiation, and activation in a number of immune and non-immune cell types (Feinberg and Jain, 2005; Li and Flavell, 2008; Shi et al., 1999). TGF-β1 is involved in the maintenance of self-tolerance and homeostasis of several T cell effectors including T regulatory cells (Fantini et al., 2004; Li et al., 2006; Wan and Flavell, 2005). Indeed, disruption of TGF-β1 or its receptors in T cells induces a severe lymphoproliferative response and autoimmunity (Marie et al., 2006; Shull et al., 1992). Thus, tight control of TGF-β1 and its downstream signaling pathways may allow for fine-tuning of the immune response by modulating T regulatory cell development or function.

Kruppel-like factors (KLFs) are a subclass of the zinc-finger family of transcription factors that participate in various aspects of cellular growth, development, and differentiation (Bieker, 1996; Feinberg et al., 2004a). KLFs are characterized by a DNA binding domain containing three $C_2H_2$-type zinc fingers capable of binding to either a CACCC-element or GC-box in the promoter region of target genes thereby regulating transcriptional activity and gene expression. Gene targeting studies have implicated important roles for KLFs in immune and hematopoietic cell biology. For example, KLF1, or EKLF (erythroid Kruppel-like factor), is expressed primarily in red blood cells. KLF1-deficient mice demonstrate defects in γ to β globin switching during erythrocyte development and, consequently, succumb to β-thalassemia (Nuez et al., 1995; Perkins et al., 1995). KLF2, or LKLF (lung Kruppel like factor), is highly expressed in single-positive T cells and targeted disruption of KLF2 verified an essential role for this factor in programming naïve T-cell quiescence (Kuo et al., 1997) and in thymic egress and peripheral trafficking. More recently, KLF4 expression was found enriched in monocytes and induced in a stage-specific manner in bone marrow progenitors; consistently, KLF4-deficiency reduced monocyte differentiation and altered myeloid cell fate potentials (Feinberg et al., 2007). Because of the importance of KLFs in different hematopoietic lineages, it was hypothesized that a related Kruppel-like zinc-finger protein may regulate the differentiation or function of $CD4^+CD25^-$ T cells and $CD4^+CD25^+$ T reg cells.

Herein, evidence is provided that in response to TGF-β1, KLF10 plays distinct roles controlling peripheral T regulatory cell differentiation, suppression function, and $CD4^+CD25^-$ T cell activation. KLF10 was initially identified in human osteoblasts as a TGF-β responsive gene (Subramaniam et al., 1995) and gene-targeting experiments in mice have verified a critical role for this factor in osteoblast-mediated mineralization and osteoblast support of osteoclast differentiation (Subramaniam et al., 2005). In vitro studies have implicated KLF10 as either a transcriptional activator or suppressor depending on the cell line in which it has been examined (Noti et al., 2004; Ribeiro et al., 1999; Tachibana et al., 1997). A recent study by Venuprasad et al. found that the E3 ubiquitin ligase Itch regulates the expression of Foxp3 and airway inflammation, in part, by enhancing the function of KLF10 (Venuprasad et al., 2008). However, the mechanisms by which KLF10 controls $CD4^+CD25^-$ T cell activation and T regulatory cell differentiation and function are unclear. KLF10 was identified as robustly expressed in T regulatory cells and is induced in $CD4^+CD25^-$ T cells in response to TGF-β in an analogous manner as Foxp3. Forced overexpression of KLF10 alone in $CD4^+CD25^-$ T cells induced Foxp3 expression, whereas KLF10-deficient $CD4^+CD25^-$ T cells have markedly reduced Foxp3 expression in response to TGF-β1. In addition, KLF10-deficient $CD4^+CD25^-$ T cells have impaired T regulatory cell differentiation, skewed cytokine profiles with enhanced Th1, Th2, and Th17 cytokines, reduced capacity to be suppressed by WT co-cultured T cell effectors, and accelerated atherosclerosis in immunodeficient, atherosclerotic $ApoE^{-/-}$/scid/scid mice. Importantly, it was found that KLF10 controls T regulatory differentiation and suppression function through distinct mechanisms. While KLF10 targets Foxp3 upon $CD4^+CD25^-$ T cell differentiation into $CD4^+CD25^+$ T regulatory cells, it promotes T regulatory cell suppression function by regulating levels of TGF-β1 and, consequently, Smad2 downstream phosphorylation, an effect independent of Foxp3 expression levels. Taken together, these observations support an important role for KLF10 as a key transcriptional regulator of peripheral T regulatory cell differentiation and suppression function and $CD4^+CD25^-$ T cell activation.

Results

Identification of KLF10 in $CD4^+CD25^+$ T Regulatory Cells and Responsiveness to TGF-β1.

Figure 1B:
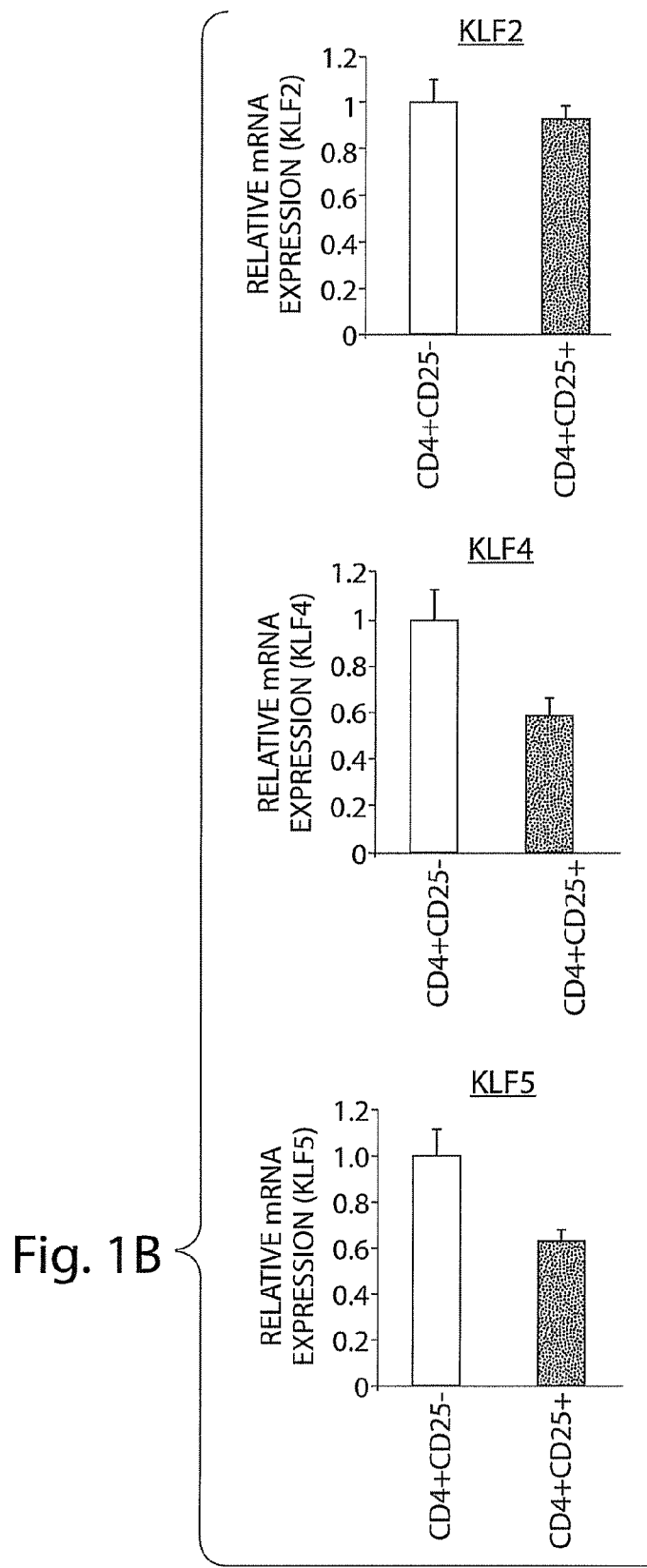
Figure 1C:
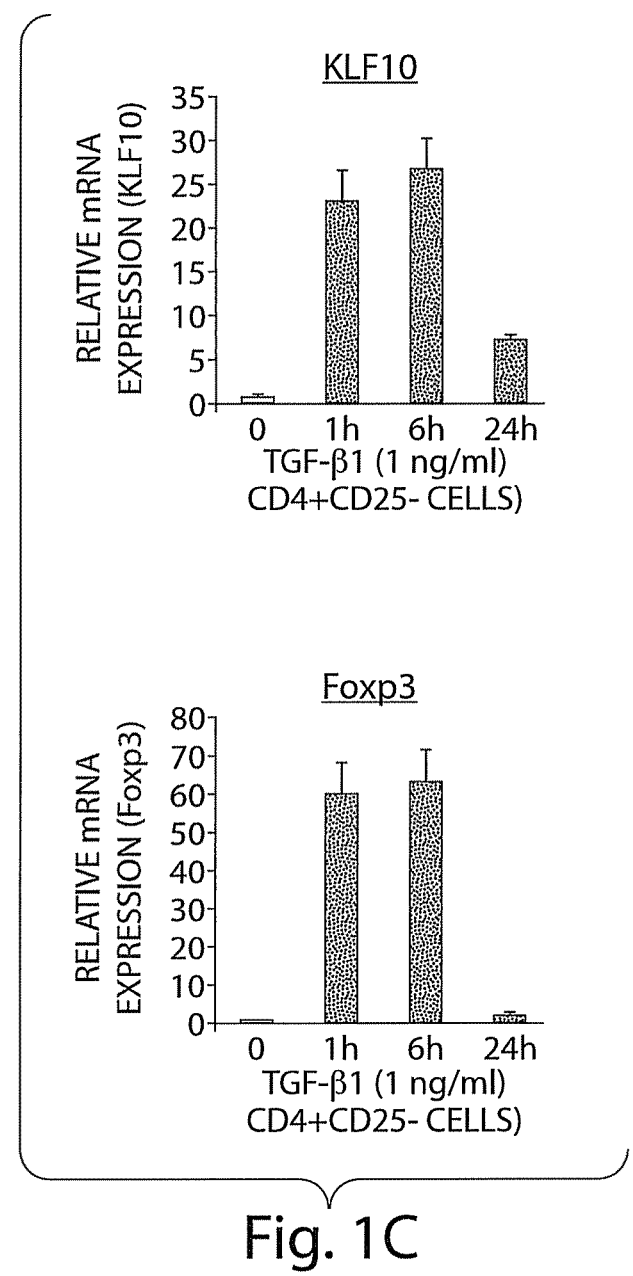
Figure 1D:
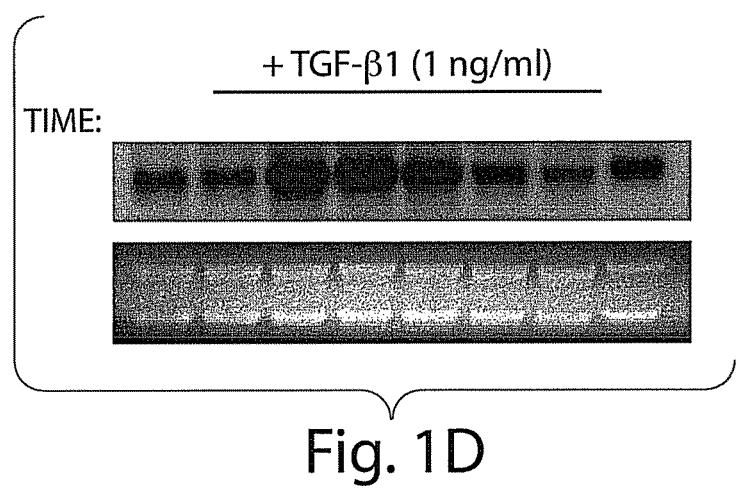
Figure 1E:
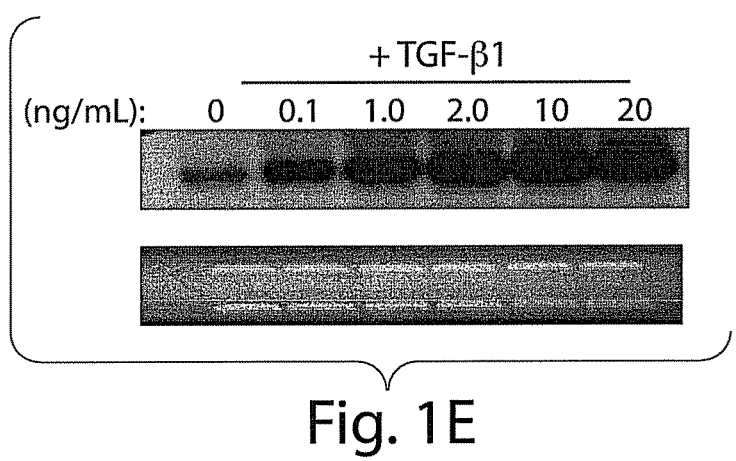
Figure 1F:
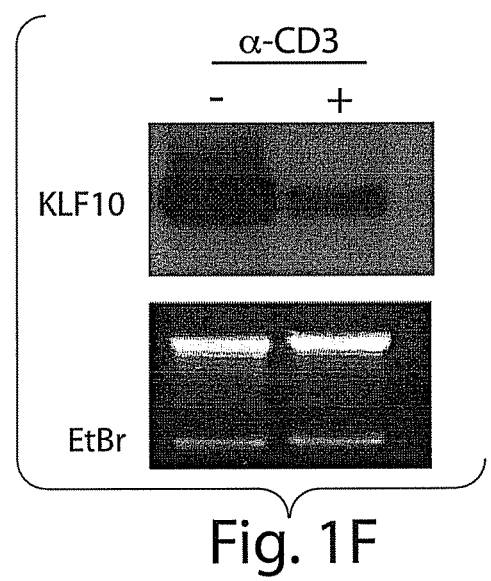
Figure 1G:
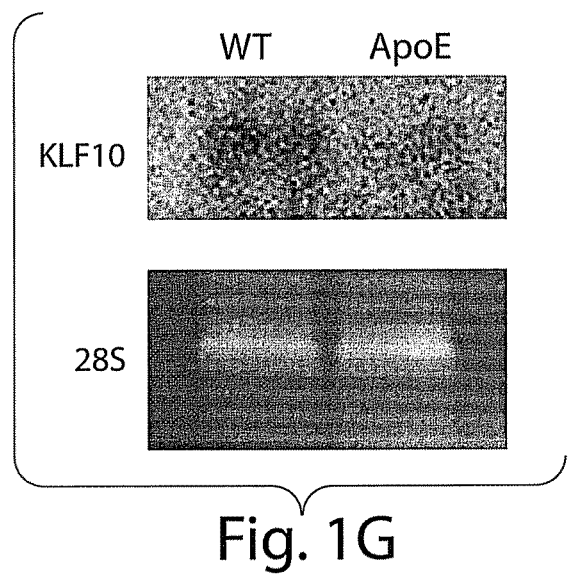

In light of the role for KLFs in other aspects of hematopoietic and immune cell biology, it was hypothesized that members of this family may also play a role in T regulatory cell biology. A panel of KLFs 1-17 were screened to find that KLF10 was robustly expressed (~6-fold) in freshly isolated, peripheral $CD4^+CD25^+$ T regulatory cells in comparison to $CD4^+CD25^-$ T cells (FIG. 1A). In contrast, other KLFs, such as KLF2, KLF4, and KLF5, were either not changed or decreased in $CD4^+CD25^+$ T regulatory cells (FIG. 1B and data not shown). One of the hallmarks of peripheral $CD4^+CD25^+$ T regulatory cells is their dependency upon TGF-β1 for their maintenance and survival (Li et al., 2006; Marie et al., 2005). $CD4^+CD25^-$ T cells can be differentiated into $CD4^+CD25^+$ T regulatory cells that express Foxp3 in vitro in the presence of TGF-β1 and anti-CD3 mAbs (Fantini et al., 2004). As shown in FIG. 1C, KLF10 mRNA was markedly induced in $CD4^+CD25^-$ T cells by ~23-fold at 1 hr, ~27-fold at 6 hr, and ~7.5-fold at 24 hrs of TGF-β1 treatment. Remarkably, TGF-β1 induced the expression pattern of the T regulatory marker, Foxp3, in an analogous pattern as KLF10. Finally, KLF10 responsiveness to TGF-β1 was also examined in the Jurkat T cell line. As demonstrated in FIGS. 1D-E, KLF10 mRNA is rapidly induced after 1 hr in Jurkat cells and can be induced in a dose-dependent manner. Collectively, these observations indicate that KLF10 expression is enriched in $CD4^+CD25^+$ T regulatory cells and can be rapidly induced in response to TGF-β1.

KLF10 Induces a T Regulatory Phenotype in $CD4^+CD25^-$ T Cells

Figure 2A:
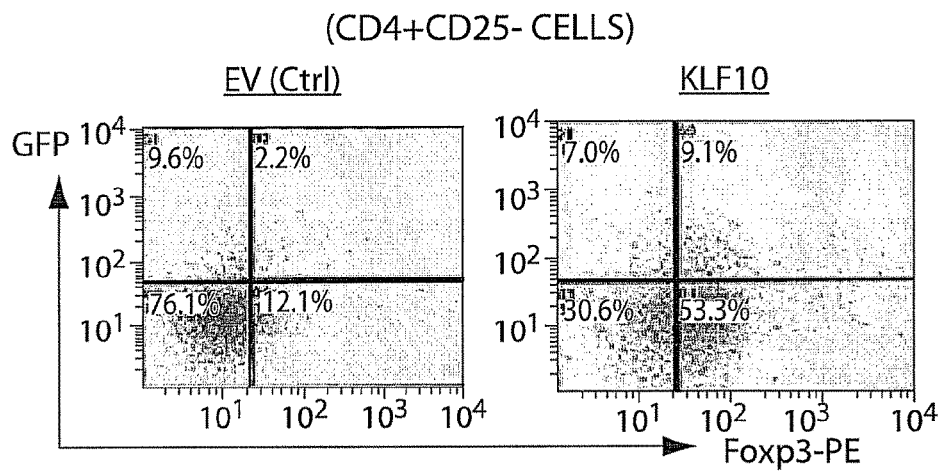
FIG. 2. Shows the effect of KLF10 overexpression on Foxp3 expression in $CD4^+CD25^-$ T cells. (A) $CD4^+CD25^-$ T cells were isolated as in FIG. 1, transduced with retrovirus GFP-RV-EV (empty-virus, ctrl) or GFP-RV-KLF10 for 72 hrs, and FACS analyses (left) were performed to assess percentage of GFP-positive cells that also expressed intracellular Foxp3. Quantification (right) of Foxp3 intracellular expression by FACS was performed from n=3 separate experiments. (B) Transduced cells from (A) were subjected to qPCR analyses for Foxp3 expression. KLF10 overexpression in $CD4^+CD25^-$ T cells induces Foxp3 mRNA expression. (C) Effects of KLF10-overexpressing $CD4^+CD25^-$ T cells on T-bet (left) and Gata3 (right) mRNA expression by qPCR analysis. (D) The growth rate of EV or KLF10-infected $CD4^+CD25^-$ T cells counted over 5 days. (E) Suppression of co-cultured $CD4^+CD25^-$ T cells by KLF10. EV or KLF10-overexpressing cells were co-cultured with $CD4^+CD25^-$ T cell effectors, α-CD3 Ab (1 μg/ml), and APCs for 72 hrs and proliferation was assessed by thymidine incorporation during the last 18 hrs. (F) KLF10-overexpressing cells promote contrasting effects on TGF-$\beta$1 and IFN-$\gamma$ expression. KLF10 promotes TGF-$\beta$1 mRNA and protein (top) as measured by ELISA from cell culture supernatants, whereas it represses IFN-$\gamma$ expression (bottom). (G) KLF10 transactivates the Foxp3 promoter and binds to DNA through an evolutionarily conserved KLF site of CCCCCCCCACCCC (SEQ ID NO:38), as determined by comparison of the Foxp3 region from human (SEQ ID NO:33), cow (SEQ ID NO:34), cat (SEQ ID NO:35), mouse (SEQ ID NO:36), and rat (SEQ ID NO:37). Transient transfection studies were performed by nucleofection (Amaxa) using $CD4^+CD25^-$ T cells. KLF10 induced the Foxp3 promoter, whereas mutation of the KLF site to CCTTTTCGAATTCC (SEQ ID NO:39) completely abolished this induction. TGF-$\beta$1 induced the Foxp3 promoter; however, mutation of the KLF site prevented the TGF-$\beta$1-mediated induction. (H) KLF10 binding to the Foxp3 promoter is dynamically regulated by TGF-$\beta$1. $CD4^+CD25^-$ T cells were subjected to chromatin immunoprecipitation (ChIP) assays using antibodies to IgG or KLF10. (I) DNAs isolated from ChIP assays were analyzed in triplicate by quantitative real-time PCR. Values were presented as relative to DNA input. (J) Effect of KLF10 expression on p21 expression and KLF10 modification.
Figure 2B:
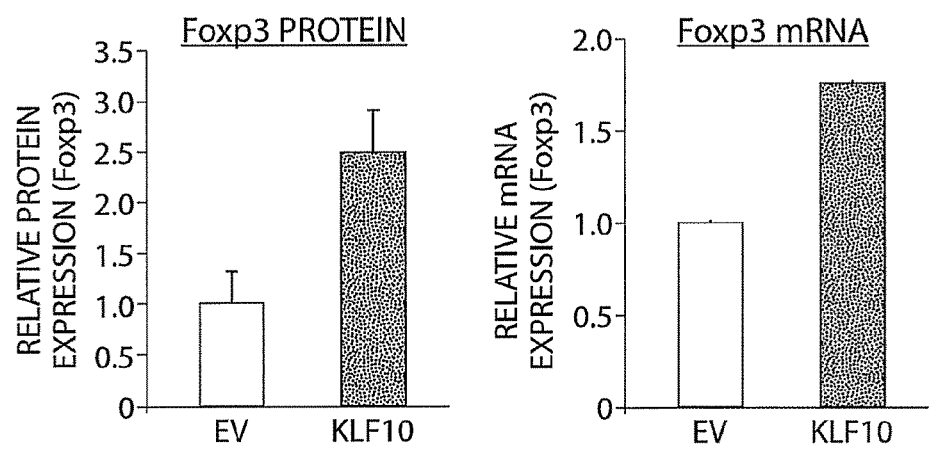
Figure 2C:
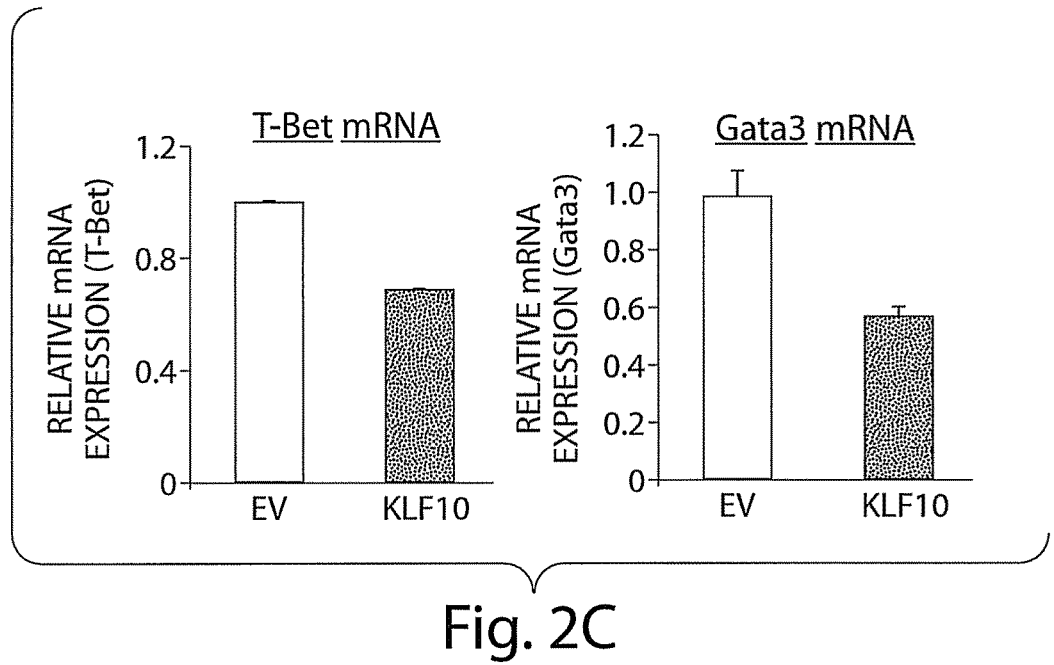
Figure 2D:
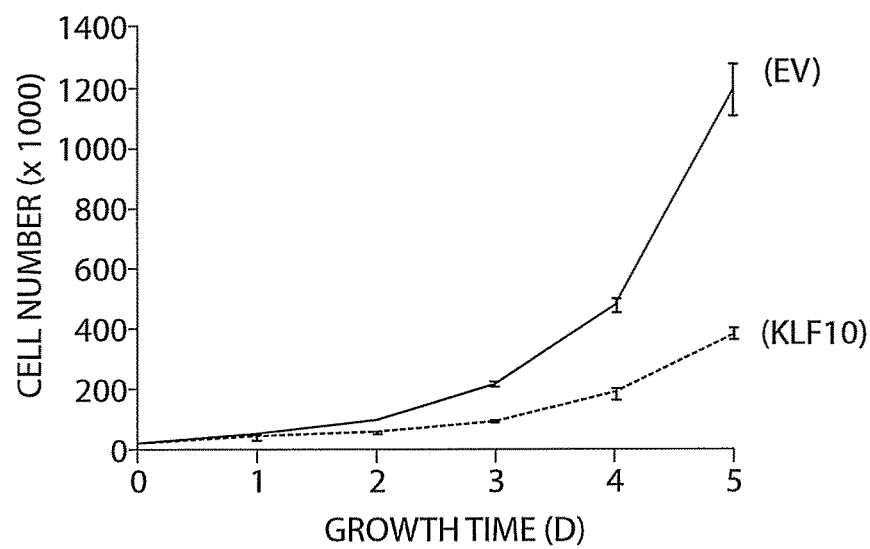
Figure 2E:
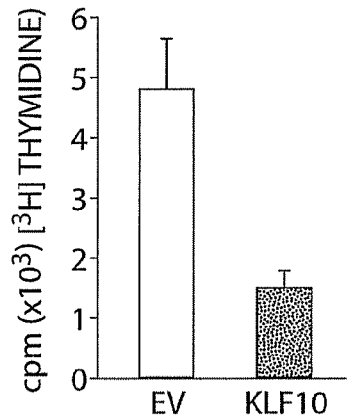
Figure 2F:
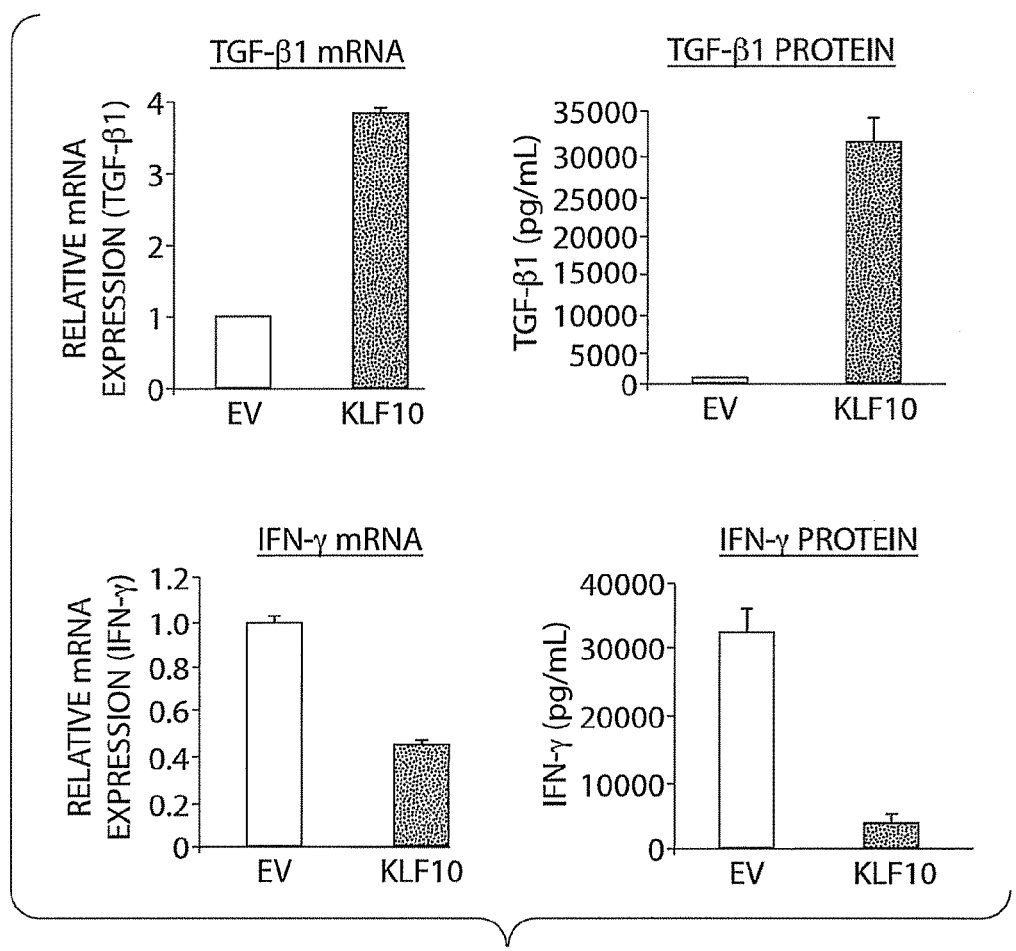
Figures 2G, 2H:
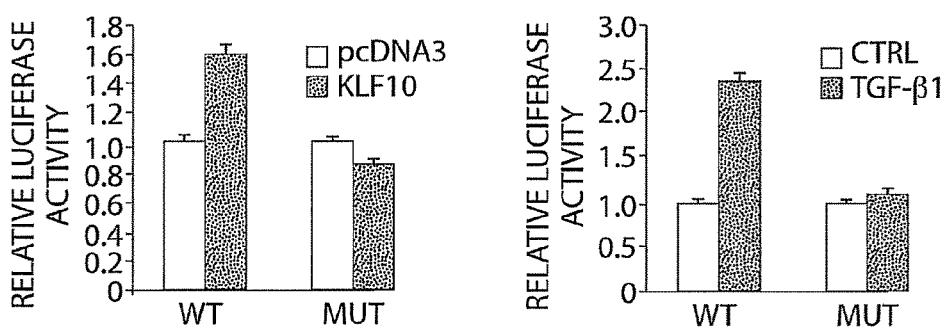
Figure 2I:
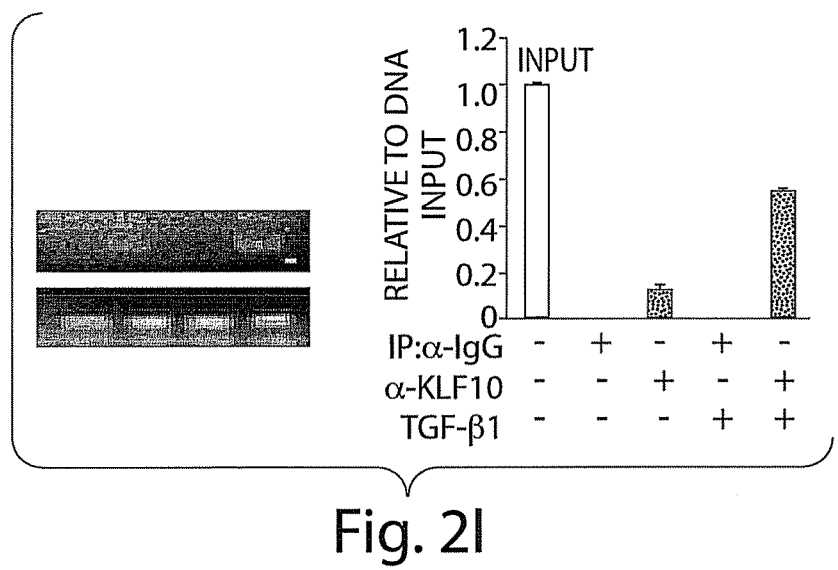
Figure 2J:
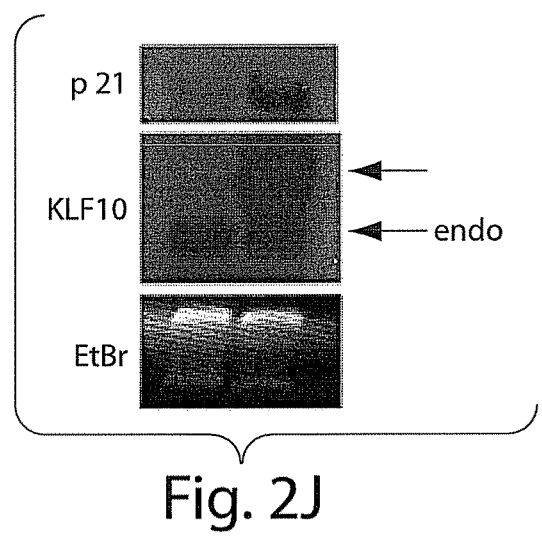
Figure 9A:
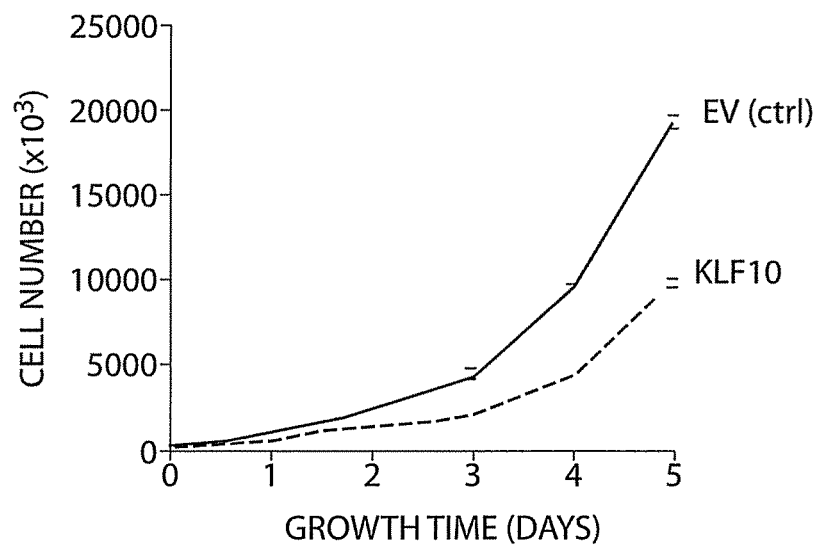
FIG. 9 depicts that overexpression of KLF10 suppresses cell growth and inhibits pro-inflammatory responses in Jurkat T cells. (A-C) Jurkat cells were retrovirally transduced with GFP-RV-EV (ctrl) or GFP-RV-KLF10 for 48 hrs, FACS-sorted for GFP-positive cells, and in (A), allowed to grow over the indicated time course. KLF10-overexpression repressed cell growth ~2-fold up to 5-days in culture and, in (B), was associated with induction of the cyclin-dependent kinase inhibitor, $p21^{WAF1CIP1}$. KLF10 (exo) is exogenous KLF10; KLF10 (endo) is endogenous KLF10. EtBr, Ethidium Bromide. (C) KLF10-overexpressing cells suppress PMA (20 ng/ml)/ionomycin (3.5 μg/mL) induction of a variety of cytokines, growth factors, and chemokines by ELISA analysis using Searchlight Multiplex protein arrays.
Figure 9B:
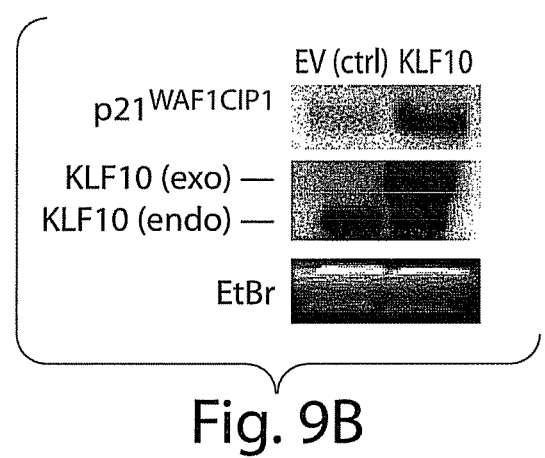
Figure 9C:
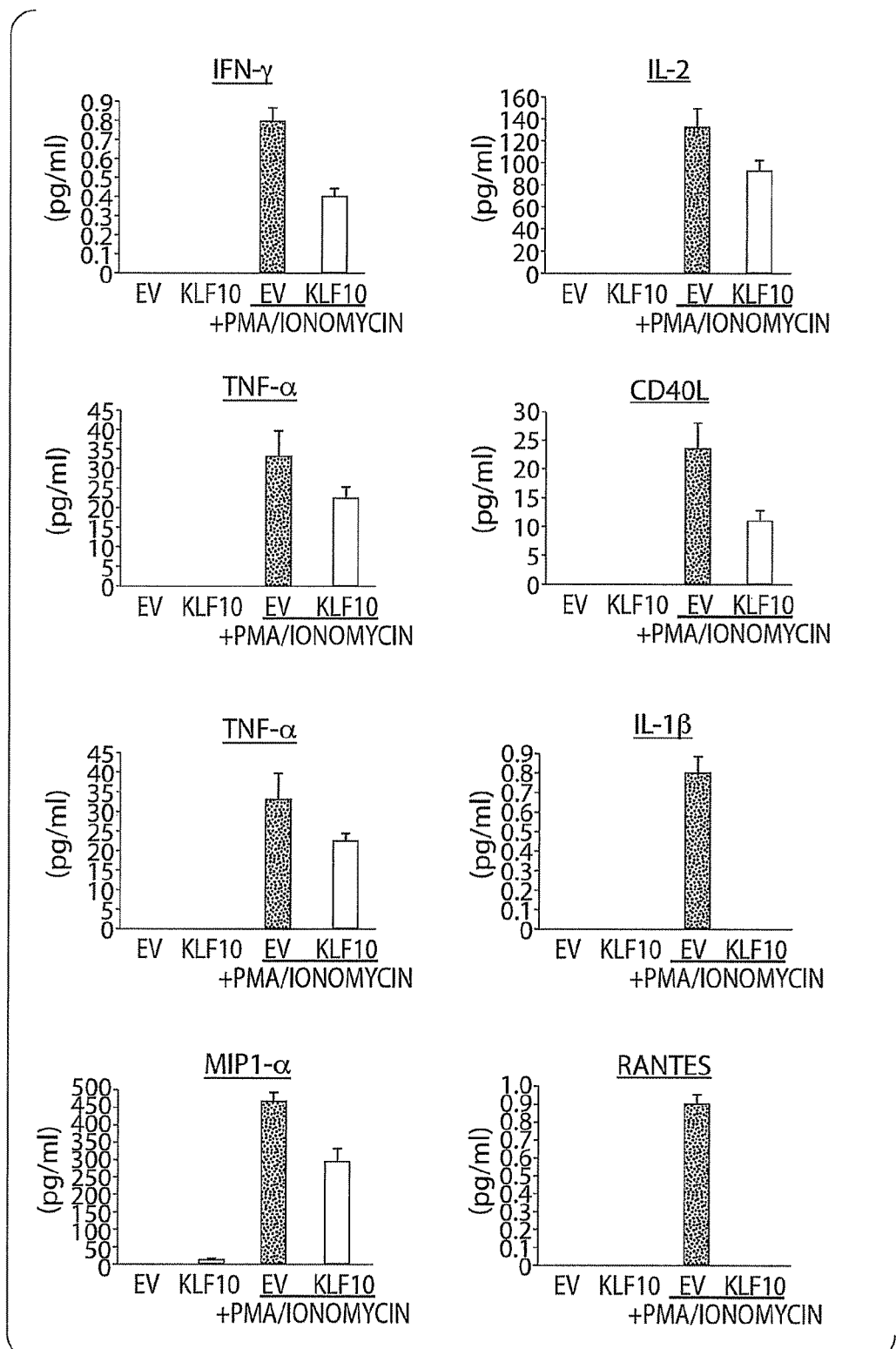

To determine whether KLF10 participates directly in T regulatory cell differentiation, $CD4^+CD25^-$ T cells were retrovirally infected with either full-length KLF10 or an empty virus control (EV) and analyzed the cells for the T regulatory marker Foxp3 four days later. In comparison to EV infected cells, there was a marked induction of Foxp3 mRNA and protein expression by flow cytometry (intracellular staining) (FIGS. 2A and B). Consistent with a T regulatory phenotype, KLF10-transduced cells also expressed lower levels of the Th1 master regulator T-bet and the Th2 master regulator Gata3 (FIG. 2C), had lower proliferative growth rates (FIG. 2D), and markedly repressed co-cultured wild-type $CD4^+CD25^-$ T responder cells activated in the presence of anti-CD3 mAb and APCs (FIG. 2E). Furthermore, KLF10-overexpressing cells suppressed the elaboration of predominantly Th1 cytokines including IFN-γ, whereas TGF-β1 levels were increased (FIG. 2F and data not shown). Similarly, overexpression of KLF10 in Jurkat cells induced cells with a quiescent phenotype. As depicted in FIG. 9, in comparison to EV ctrl cells, KLF10-overexpressing cells decreased cell growth by ~2-fold over 5-days, induced $p21^{WAF1}$, and inhibited a range of pro-inflammatory cytokines and growth factors, including IL-2 and IFN-γ, in response to PMA/ionomycin. Finally, to define the mechanism(s) underlying the ability of KLF10 to induce expression of Foxp3, transient transfection studies were performed using the Foxp3 promoter. A ~1.5-fold induction of the Foxp3 promoter by KLF10 (FIG. 2G)

was observed. Members of the Kruppel-like family bind to specific DNA elements (5'-CNCCC-3') to exert their function. Mutation of an evolutionarily conserved CACCC KLF DNA-binding site abolished the KLF10-mediated induction of the Foxp3 promoter (FIG. 2G). Consistently, TGF-β1 induced the Foxp3 promoter by ~2.4-fold and mutation of the KLF10 DNA-binding site also prevented TGF-β1-mediated induction of the Foxp3 promoter. To assess the ability of KLF10 to bind DNA to this site within the Foxp3 promoter, chromatin immunoprecipitation (ChIP) studies were performed using CD4$^+$CD25$^-$ T cells stimulated in the presence of anti-CD3 Abs and TGF-β1. As shown in FIG. 2H-I, in response to TGF-β1, KLF10 potently bound to this site ~4-fold over basal levels as measured by qPCR. Taken together, these data indicate that KLF10 can promote the acquisition of a T regulatory cell phenotype.

Figure 3A:
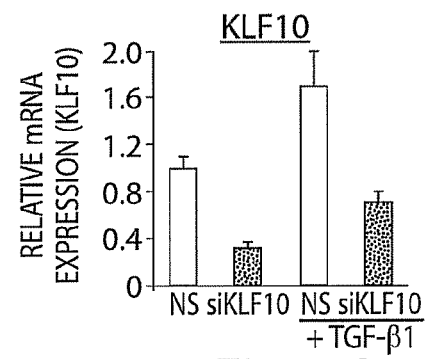
FIG. 3 shows the effect of KLF10-deficiency in $CD4^+CD25^-$ T cells on Foxp3 expression, T regulatory cell development, and Th1/Th2 differentiation. (A-B) $CD4^+CD25^-$ cells were transfected with siRNA for NS (non-specific scrambled siRNA) or KLF10 (siKLF10) by nucleofection technique (Amaxa) and harvested 48 hrs later for qPCR analysis after 6 hrs of treatment with vehicle Ctrl or TGF-$\beta$1 (1 ng/ml). KLF10 'knockdown' (A) reduces Foxp3 mRNA expression in response to TGF-$\beta$1 (B). (C) $CD4^+CD25^-$ cells transfected cells (NS or siKLF10) were grown for 72 hrs. KLF10-knockdown promoted cell growth by ~33% vs. NS Ctrl. (D) In response to TGF-$\beta$1, Foxp3 mRNA expression is reduced in KLF10−/− $CD4^+CD25^-$ T cells. WT or KLF10−/− $CD4^+CD25^-$ T cells were treated with anti-CD3 Abs and TGF-$\beta$1 for 24 hours followed by qPCR analysis. (E) KLF10−/− mice have markedly reduced peripheral $CD4^+CD25^+$ and $CD4^+CD25^+Foxp3^+$ T regulatory cells. Spleen and mesenteric lymph nodes from littermate, day 10 male KLF10−/− and WT mice (n=4/group) were analyzed by FACS for percentage of $CD4^+CD25^+$ and $CD4^+CD25^+Foxp3^+$ T regulatory cells. (F) KLF10−/− $CD4^+CD25^-$ T cells differentiate more readily along Th1 and Th2 pathways than WT $CD4^+CD25^-$ T cells. $CD4^+CD25^-$ T cells were treated along Th1- or Th2-skewing conditions for up to 3 days. (Top) The Th1 markers T-Bet and IFN-$\beta$1 were assessed by qPCR and ELISA, respectively; (bottom) the Th2 markers Gata3 and IL-5 were assessed by qPCR and ELISA, respectively.
Figure 3B:
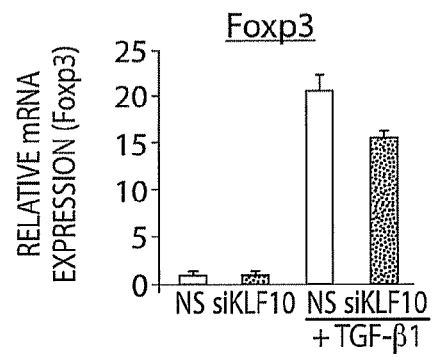
Figure 3C:
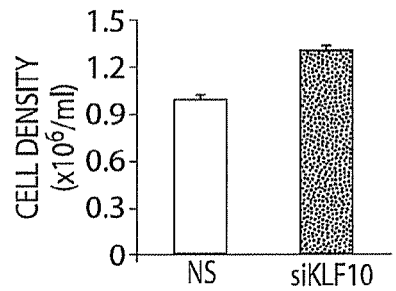
Figure 3D:
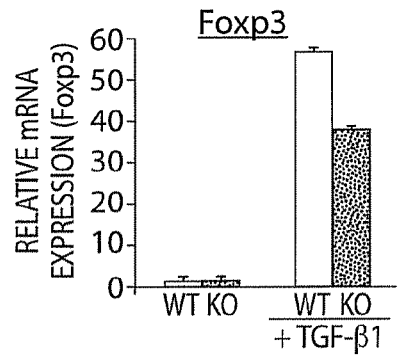
Figure 3E:
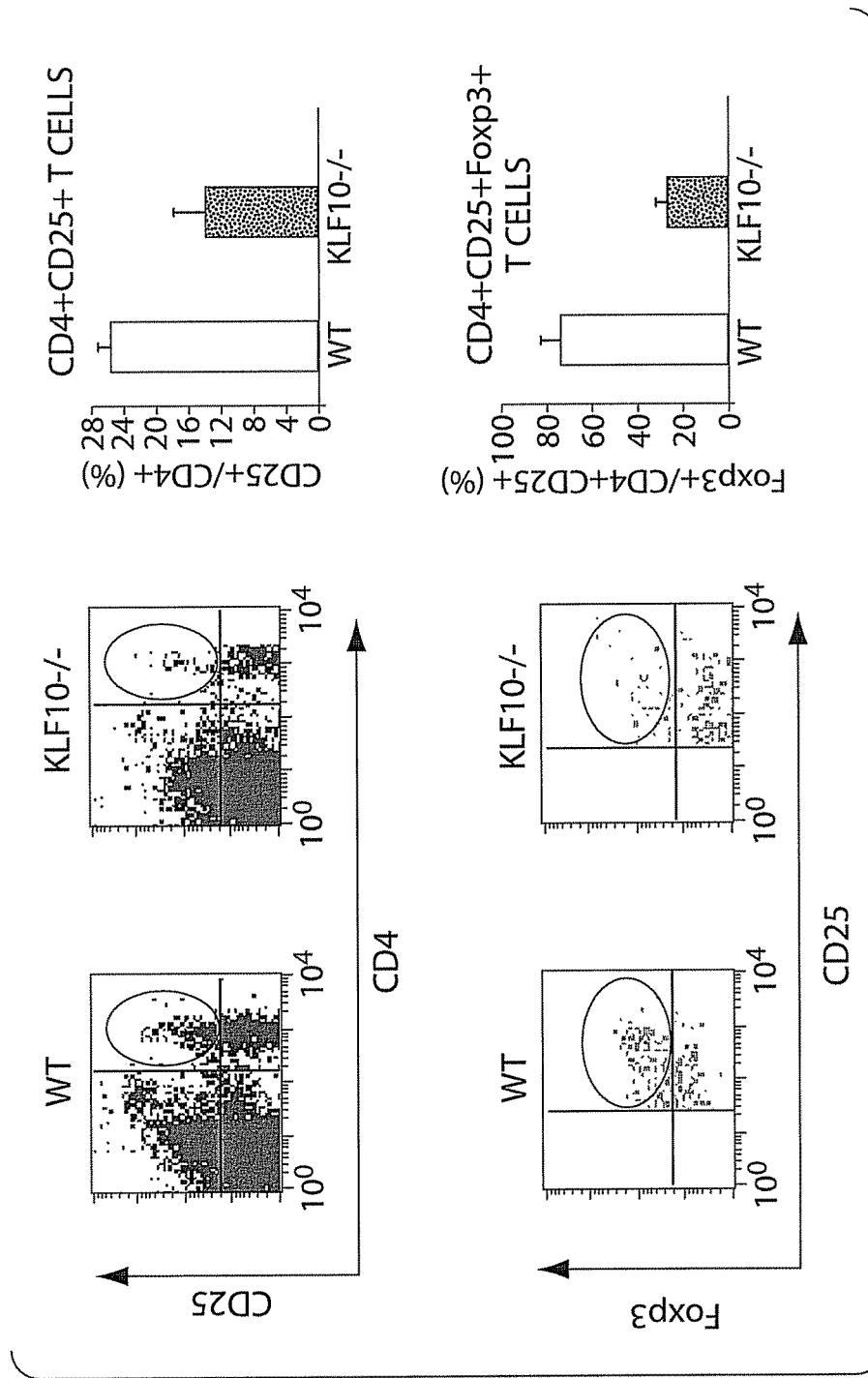
Figure 3F:
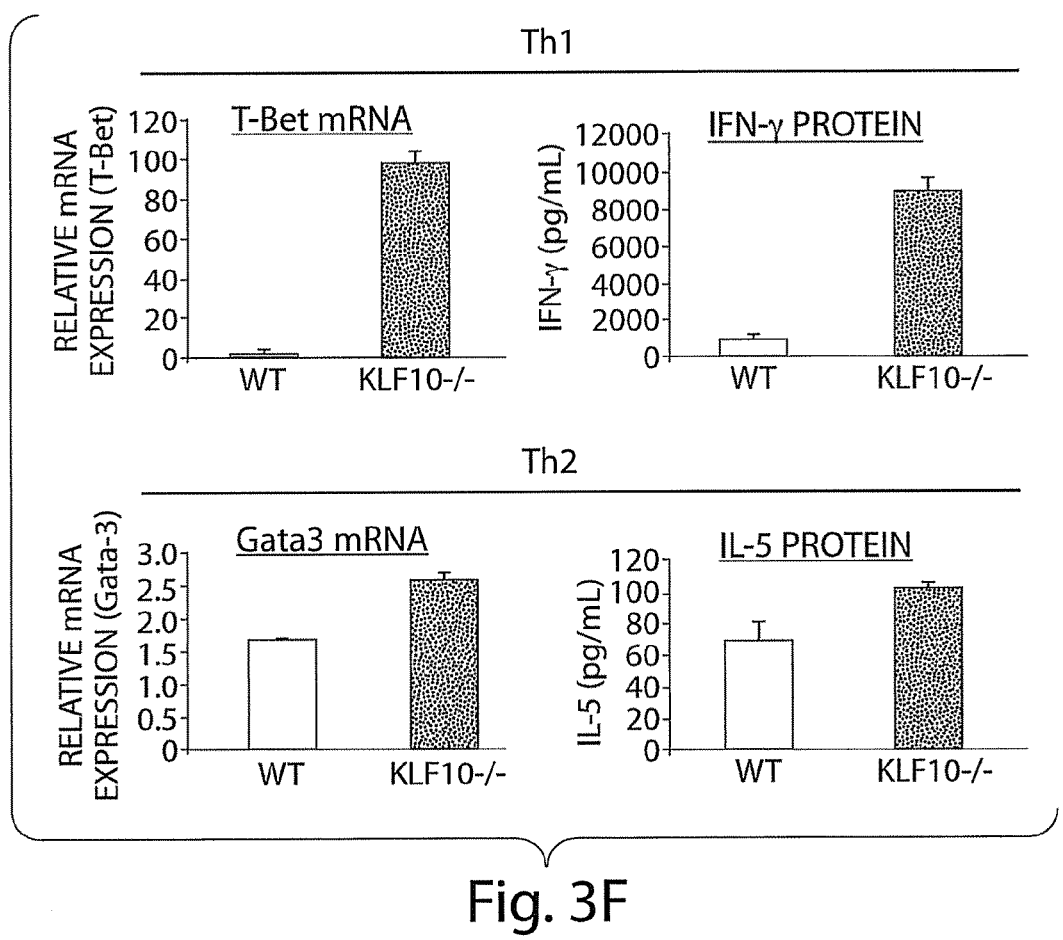

KLF10 Deficiency Impairs Foxp3 Expression, T Regulatory Cell Development, and Alters Th1 and Th2 Differentiation Because overexpression of KLF10 alone promoted T regulatory cell differentiation in primary CD4$^+$CD25$^-$ T cells, it was hypothesized that KLF10 deficiency may reduce the induction of Foxp3 expression and possibly alter the functional capacity of CD4$^+$CD25$^+$ T regulatory cells. As a first step in understanding whether KLF10-deficiency may affect Foxp3 expression, short interfering (si)-RNA oligonucleotides were used to knockdown endogenous KLF10 expression in primary CD4$^+$CD25$^-$ T cells in the presence or absence of TGF-β1 treatment. As shown in FIG. 3A, endogenous KLF10 expression was reduced ~55% and ~65% in the presence or absence of TGF-β treatment, respectively. Interestingly, knockdown of KLF10 inhibited the induction of Foxp3 in response to TGF-β by ~27% (FIG. 3B). Furthermore, in contrast to the diminished proliferative properties of KLF10-overexpressing cells (FIG. 2D), KLF10-'knockdown' CD4$^+$CD25$^-$ T cells grew more avidly in response to T cell activation with anti-CD3 mAbs than wild-type controls (FIG. 3C). Moreover, CD4$^+$CD25$^-$ T cells isolated from KLF10-/-0 mice had impaired induction of Foxp3 mRNA in response to TGF-β1 in comparison to WT CD4$^+$CD25$^-$ T cells (FIG. 3D). Finally, to assess whether the complete absence of KLF10 alters T regulatory cell development, the percentage of peripheral T regulatory cells from wild-type (WT) or KLF10-/- mice were assessed. As shown in FIG. 3E, KLF10-/- mice had ~50% and ~67% reductions in peripheral CD4$^+$CD25$^+$ T cells and CD4$^+$CD25$^+$Foxp3$^+$ T regulatory cells, respectively, in comparison to WT mice. Previous reports demonstrate that relative Foxp3-deficiency may alter the balance along CD4$^+$ Th1 or Th2 differentiation pathways (Zheng and Rudensky, 2007; Ziegler, 2006). To explore if KLF10-deficient cells have enhanced skewing along these pathways, WT or KLF10-/- CD4$^+$CD25$^-$ T cells were treated under Th1 or Th2 skewing conditions as described (Bettelli et al., 2006). As shown in FIG. 3F, KLF10-/- CD4$^+$CD25$^-$ cells had markedly enhanced differentiation along Th1 and Th2 pathways including increased expression of Th1 markers, T-bet and IFN-γ, and Th2 markers, Gata3 and IL-5. Collectively, these observations indicate that the presence of KLF10 is important for modulating both Foxp3 expression levels, peripheral T regulatory cell development, and CD4$^+$CD25$^-$ Th1 and Th2 differentiation pathways. KLF10-/- T regulatory cells have impaired suppression function that can be restored by exogenous TGF-β1

Figure 4A:
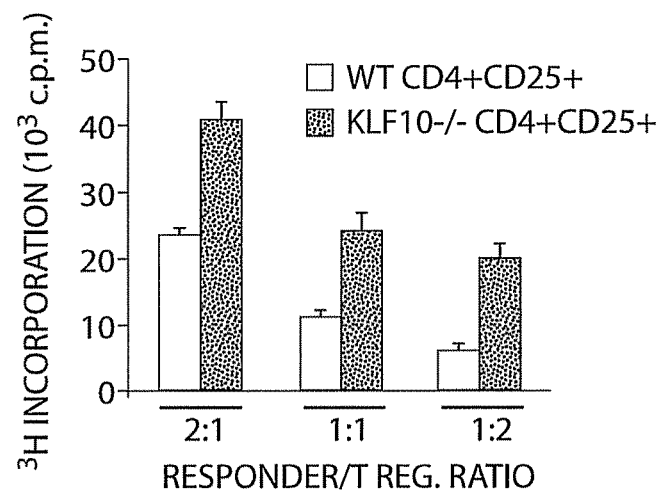
FIG. 4 depicts the effect of KLF10-deficiency on $CD4^+CD25^+$ T regulatory cell function. (A) KLF10−/− $CD4^+CD25^+$ T regs have markedly impaired suppression function. Equal numbers of WT or KLF10−/− $CD4^+CD25^+$ T regs were co-cultured with WT $CD4^+CD25^-$ T cell effectors, α-CD3 Ab (0.25 μg/ml), and APCs for 72 hrs and proliferation was assessed by thymidine incorporation during the last 18 hrs. (B) Gene-dosage effect of KLF10-deficiency on T reg suppression function. Equal numbers of WT, KLF10+/−, or KLF10−/− $CD4^+CD25^+$ T regs were subjected to suppression assays as described in (A). (C) Reduced levels of TGF-$\beta$1 elaboration in KLF10−/− $CD4^+CD25^+$ and $CD4^+CD25^+Foxp3^+$ T regs. FACS-purified T regs were stimulated by α-CD3 Abs for 24 hrs. After stimulation, culture supernatants were harvested and assessed by SearchLight Proteome Arrays/multiplex sandwich ELISA for TGF-$\beta$1. D) Rescue of KLF10−/− T regulatory cell suppression function by exogenous TGF-$\beta$1. $CD4^+CD25^+$ T regs (left) or $CD4^+CD25^+Foxp3^+$ T regs (right) were isolated from WT or KLF10−/− mice and suppression assays were performed in the presence of α-CD3 Ab, APCs, and TGF-$\beta$1 (1 ng/ml) as described in (A). (E) KLF10−/− T regs have defective TGF-β1 signaling. WT and KLF10−/− CD4+CD25+ T regs were stimulated with anti-CD3 Abs and TGF-β1 (1 ng/ml) for 1 hr and Western blot analyses performed for the indicated proteins. KLF10−/− T regs have markedly reduced levels of phosphorylated Smad2. Data are representative of three independent experiments and similar results were obtained as quantitated by densitometry of the bands (right).
Figure 4B:
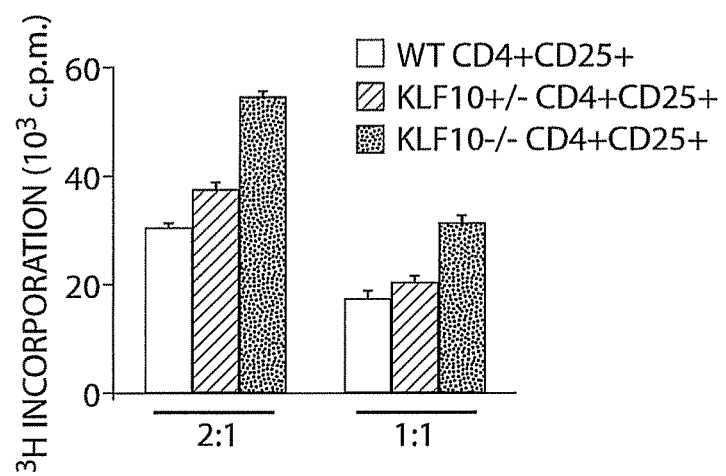
Figure 4C:
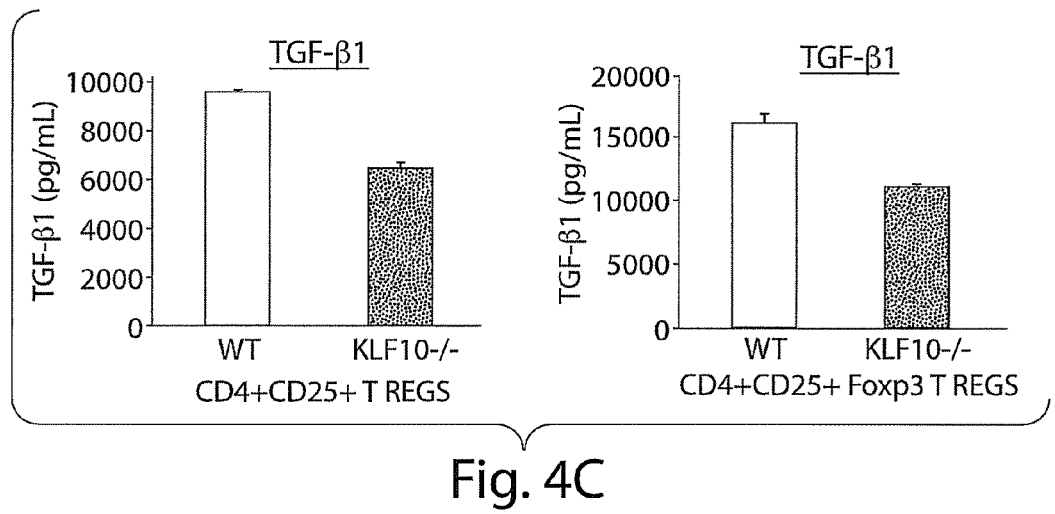
Figure 4D:
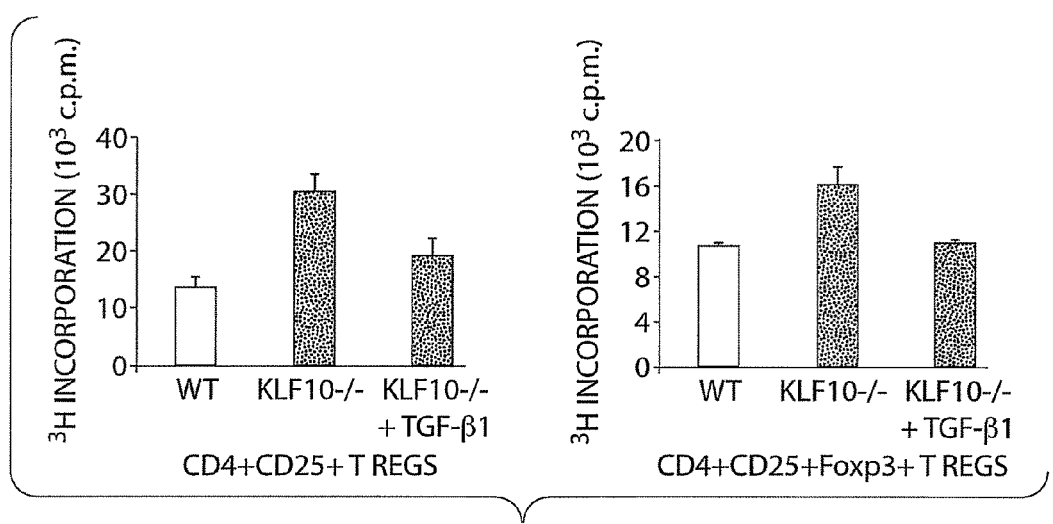
Figure 4E:
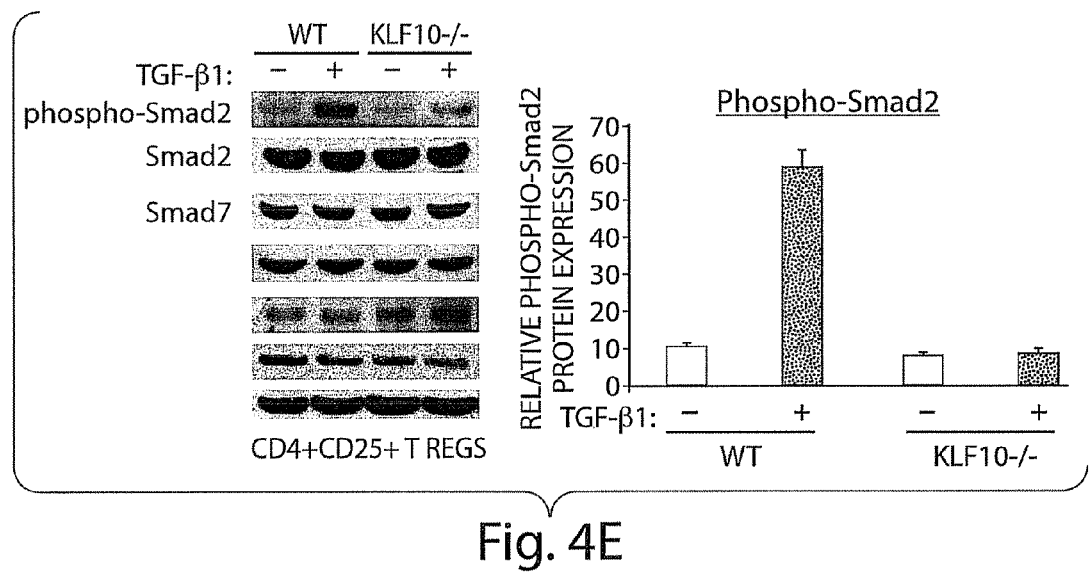

While KLF10-/- mice have reduced peripheral T regs, an important question is whether they may be functionally impaired. To assess whether the absence of KLF10 alters T regulatory cell function, isolated equal numbers of CD4$^+$CD25$^+$ T regulatory cells from WT or KLF10-/- mice were isolated and suppression assays were performed with co-cultured wild-type CD4$^+$CD25$^-$ T cell responders. As shown in FIG. 4A, KLF10-/- CD4$^+$CD25$^+$ T regs had up to ~67% reduced suppression function of co-cultured CD4$^+$CD25$^-$ T cells grown in the presence of APCs and anti-CD3 mAbs in comparison to WT CD4$^+$CD25$^+$ T regs. Indeed, a gene-dosage effect in suppression function was observed (FIG. 4B) across WT, KLF10+/-, and KLF10-/- CD4$^+$CD25$^+$ T regs, an effect suggesting that tight control of KLF10 expression may be important for T regulatory cell suppression function. Emerging studies implicate TGF-β1 as a critical mediator of T regulatory cell suppressor function (Bommireddy and Doetschman, 2007) (Li and Flavell, 2008; von Boehmer, 2005). To assess if KLF10-/- T regulatory cells have impaired release of TGF-β1, supernatants of WT or KLF10-/- CD4$^+$CD25$^+$ and CD4$^+$CD25$^+$Foxp3$^+$ T regulatory cells were isolated and were found to have a ~32% and 34% reduction in TGF-β1 secretion, respectively (FIG. 4C). Furthermore, KLF10-/- CD4$^+$CD25$^+$ T regulatory cells have ~40% reduced TGF-β1 mRNA levels compared to WT T regs (data not shown). These observations raise the possibility that exogenous administration of TGF-β1 may, in part, rescue the defect in TGF-β1 release observed in KLF10-/- T regs and allow for more complete suppression of co-cultured T cell effectors. As demonstrated in FIG. 4D, KLF10-/- CD4$^+$CD25$^+$ and CD4$^+$CD25$^+$Foxp3$^+$ T regs suppressed co-cultured WT CD4$^+$CD25$^-$ T cell effectors markedly lower (~58% and ~60% reduced, respectively) in comparison to WT CD4$^+$CD25$^+$ and CD4$^+$CD25$^+$Foxp3$^+$ T regs. Remarkably, exogenous administration of TGF-β1 (1 ng/ml) rescued the defect in suppression function in both KLF10-/- CD4$^+$CD25$^+$ T regs and CD4$^+$CD25$^+$Foxp3$^+$ T regs to near levels achieved by WT CD4$^+$CD25$^+$ T regs. Finally, because KLF10-/- T regs have reduced elaboration of TGF-β1, it was hypothesized that TGF-β signaling may be impaired in KLF10-/- T regs. Cellular signaling through the TGF-β superfamily occurs via intracellular mediators, termed Smads, which translocate to the nucleus, where they direct transcriptional responses (Shi and Massague, 2003). Three classes of Smads (pathway-restricted, common, and inhibitory) are responsible for propagating the downstream signaling effects. TGF-β/activin receptors phosphorylate the pathway-restricted Smads, Smad2 and Smad3, whereas bone morphogenic protein receptors activate Smad1, Smad5, and Smad8. Pathway-restricted Smads may hetero-oligomerize with the only common Smad, Smad4, before translocating to the nucleus. The inhibitory Smads, Smad6 and Smad7, are structurally divergent from other Smads and function to block TGF-β signaling by preventing ligand-induced receptor phosphorylation of pathway-restricted Smads. Indeed, as shown in FIG. 4E, KLF10-/- T regs stimulated with anti-CD3 Abs and TGF-β1 for 1 hr had profoundly reduced levels of phosphorylated Smad2, whereas there were no differences in the expression of Smad2, Smad7, the TGF-β1 and II type receptors, and Foxp3. Thus, KLF10-/- T regs have altered T regulatory suppressive function largely as a consequence of reduced elaboration of TGF-β1.

KLF10-/- CD4$^+$CD25$^-$ T Cells are hyperactivated and Promote Atherosclerosis

Figure 5A:
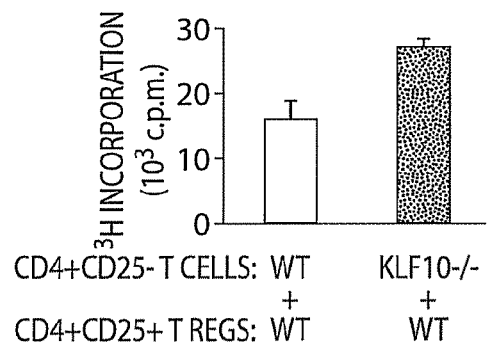
FIG. 5 shows that KLF10−/− CD4+CD25− T cells are hyperactivated and promote atherosclerosis. (A) WT or KLF10−/− CD4+CD25− T cell effectors were FACS-purified and subjected to suppression assays using WT CD4+CD25+ T regs in the presence of anti-CD3 Abs and APCs for 72 hrs and proliferation was assessed by thymidine incorporation during the last 18 hrs. WT T regs suppress KLF10−/− CD4+CD25− T cells less effectively than WT CD4+CD25− T cell effectors. (B) KLF10−/− CD4+CD25− T cells are hyperactivated in response to TCR stimulation. WT or KLF10−/− CD4+CD25− T cells were stimulated with anti-CD3 Abs for 24 hrs and subjected to qPCR analyses for the indicated cytokines. (C) After stimulation in (B), culture supernatants were harvested and assessed by SearchLight Proteome Arrays/multiplex sandwich ELISA for the indicated cytokines. Each sample was evaluated in triplicate and is representative of two independent experiments. (D) KLF10−/− CD4+CD25− T cells promotes atherosclerotic lesion formation in ApoE−/−/scid/scid mice. WT or KLF10−/− CD4+CD25− T cells were transferred intravenously into ApoE−/−/scid/scid mice (n=5 recipient mice for WT cells; n=7 recipient mice for KLF10−/− cells), placed on a high fat diet for five weeks, and aortic root lesion size ($\mu m^2$) was quantitated morphometrically after Oil Red O staining (left). Quantitation of staining for CD4+ T cells and Mac3+ macrophages (Right). Data were obtained by counting lesions at the aortic root from 5 to 7 mice of each group. (E) Plasma levels of pro-inflammatory mediators increased, whereas TGF-β1 levels decreased in recipient ApoE−/−/scid/scid adoptively transferred with KLF10−/− CD4+CD25− T cells. Plasma from ApoE−/−/scid/scid mice receiving WT or KLF10−/− CD4+CD25− T cells was collected and assessed by SearchLight Proteome Arrays/multiplex sandwich ELISA as in (B). (F) KLF10−/− CD4+CD25− T cells have defective TGF-β1 signaling. WT and KLF10−/− CD4+CD25− T cells were stimulated with anti-CD3 Abs and TGF-β1 (1 ng/ml) for 1 hr and Western blot analyses performed for the indicated proteins. KLF10−/− CD4+CD25− T cells have markedly reduced levels of phosphorylated Smad2. Data are representative of three independent experiments and similar results were obtained as quantitated by densitometry of the bands (right).

While KLF10-/- T regs have impaired suppression function of wild-type T cell effectors, the converse question is equally important. In comparison to WT CD4$^+$CD25$^-$ T cell effectors, can KLF10-/- CD4$^+$CD25$^-$ T cell effectors be equally suppressed by WT T regs? To examine this, suppression assays were performed using WT CD4$^+$CD25$^+$ T regs co-cultured with WT or KLF10-/- CD4$^+$CD25$^-$ T cell effectors. As shown in FIG. 5A, WT T regs suppressed KLF10-/-

Figure 5B:
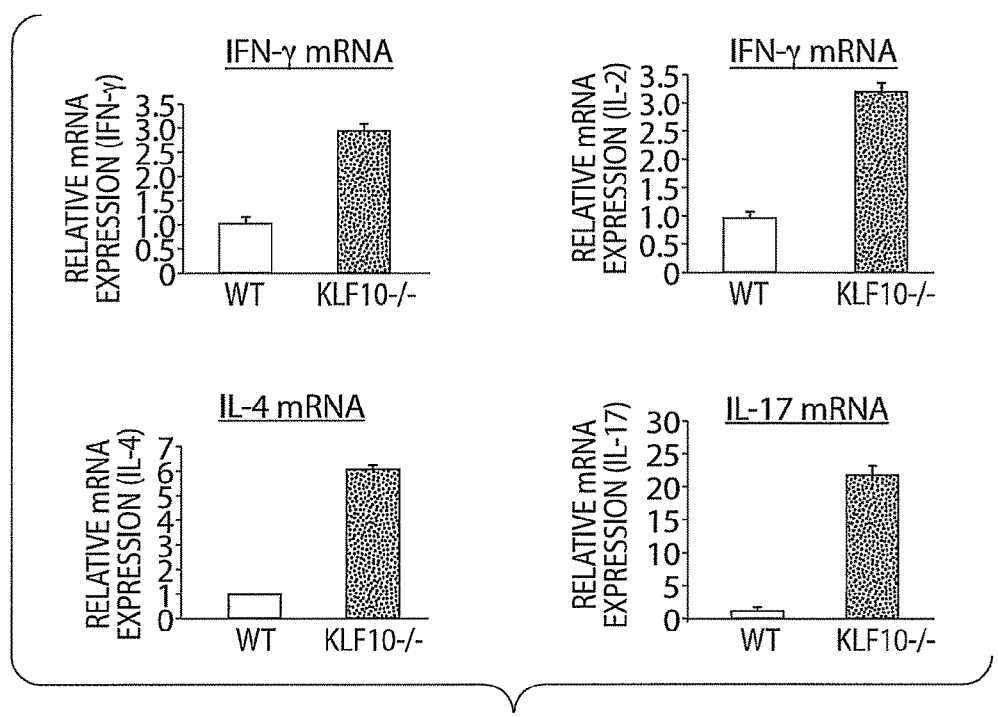
Figure 5C:
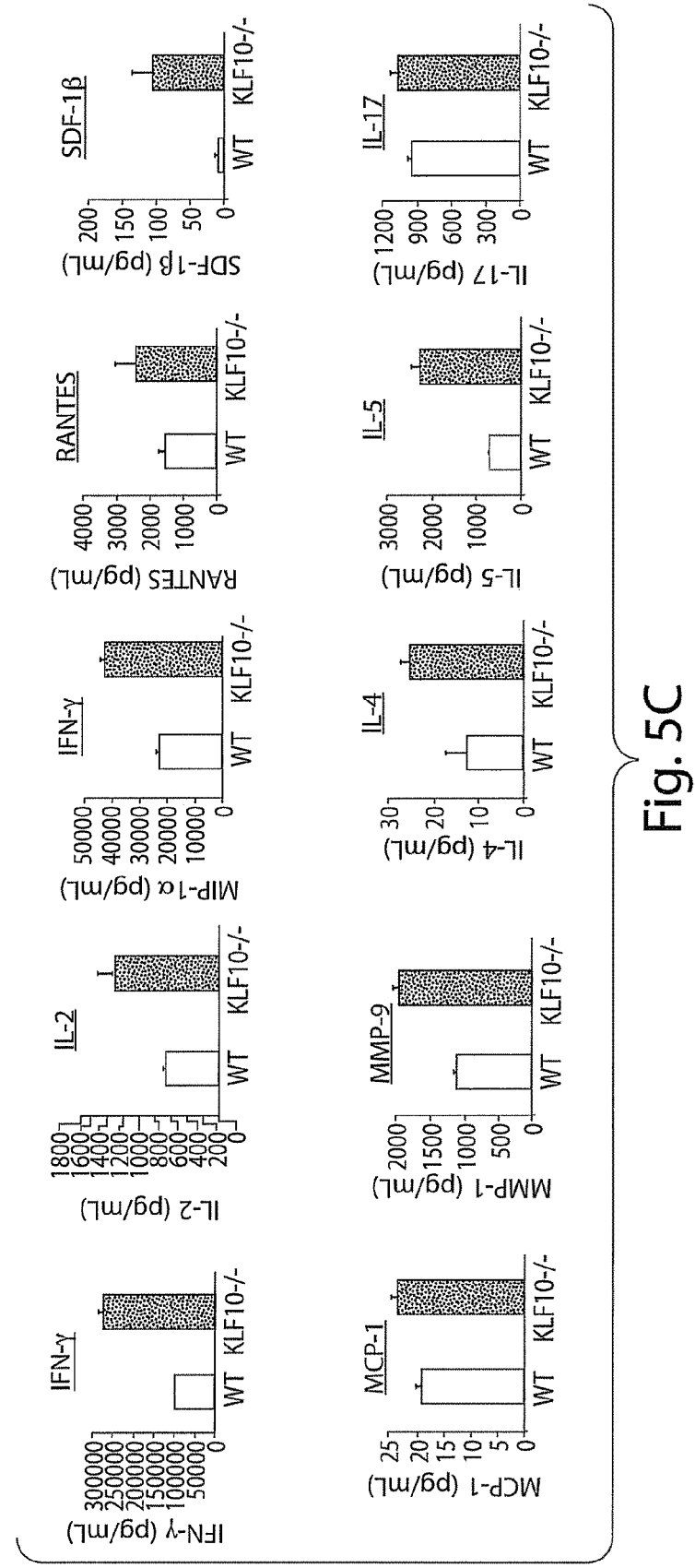
Figure 5D:
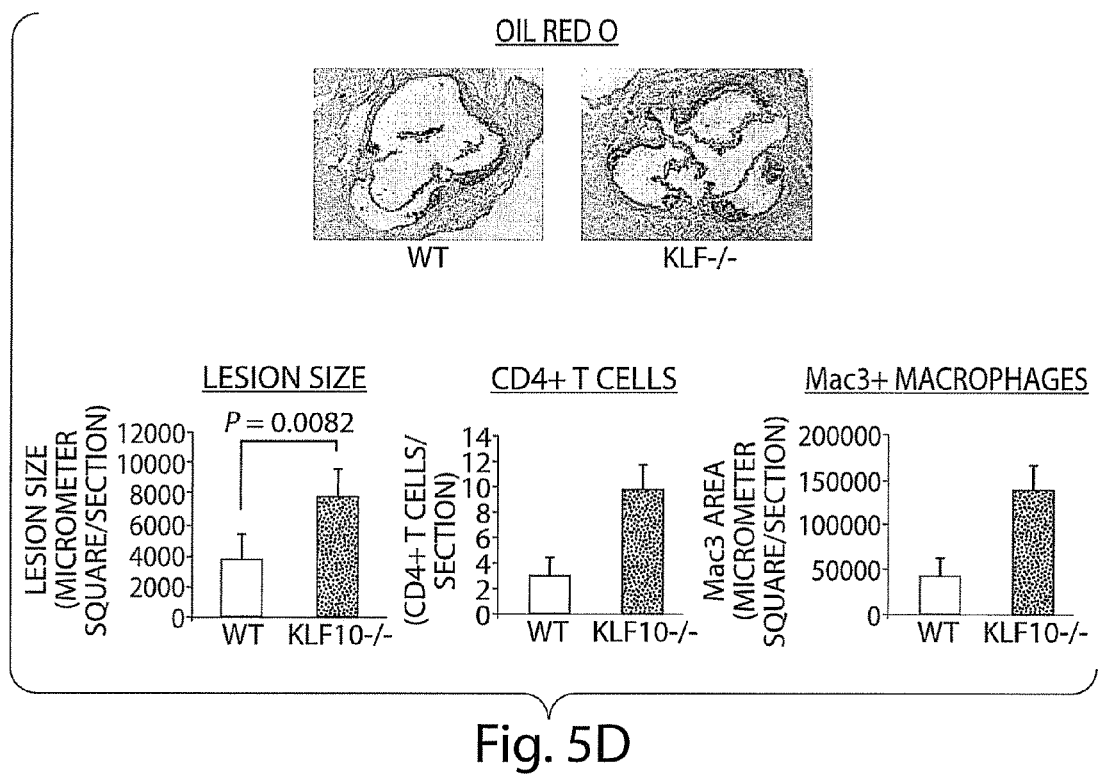
Figure 5E:
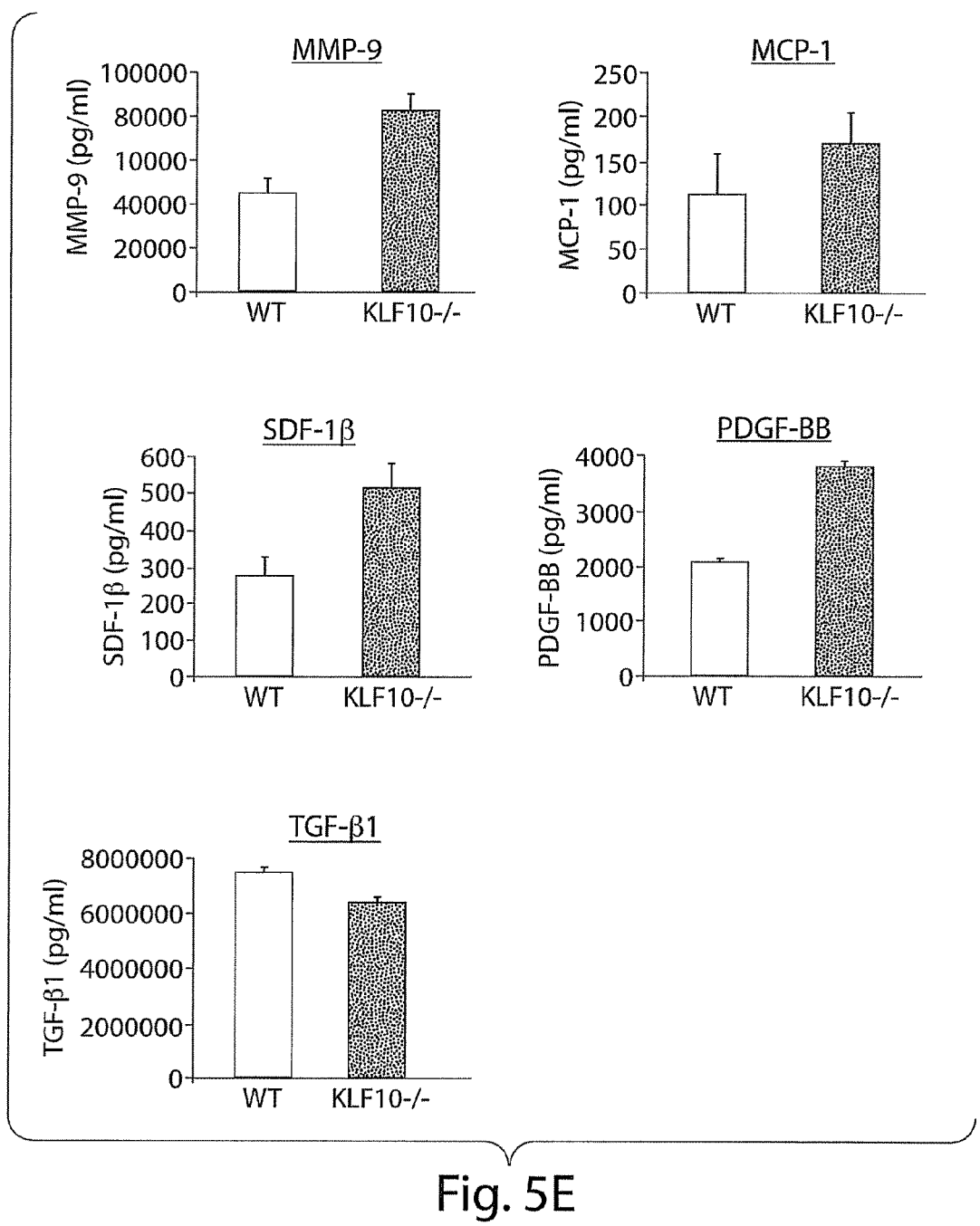

CD4$^+$CD25$^-$ T cell effectors less potently (~41% lower) in comparison to WT CD4$^+$CD25$^-$ T cell effectors, an effect suggesting that KLF10−/− CD4$^+$CD25$^-$ T cells may be 'hyperactivated' with altered elaboration of Th1, Th2, or Th17 cytokines. As a first step to explore this possibility, mRNAs for Th1, Th2, and Th17 markers were examined. Indeed, in response to anti-CD3 Abs, KLF10−/− CD4$^+$CD25$^-$ T cells robustly increased mRNAs for IFN-γ and IL-2 (Th1), IL-4 (Th2), and IL-17 (Th17)(FIG. 5B). Consistently, upon TCR activation, enhanced elaboration of several cytokines in KLF10−/− CD4$^+$CD25$^-$ T cells including Th1 (ie. IFN-γ, IL-2), Th2 (ie. IL-4, IL-5), and Th17 (ie. IL-17) (FIG. 5C) were found. In particular, a number of IFN-γ responsive proteins including MIP1-α, MIP1-β, RANTES, and SDF-1β, eotaxin, MCP-1, and MMP-9 were potently induced in KLF10−/− CD4$^+$CD25$^-$ T cells. Interestingly, increased levels of several of these chemokines/factors are associated with the development or progression of chronic inflammatory diseases such as atherosclerosis (Hansson and Libby, 2006). To assess the functional contribution of CD4$^+$CD25$^-$ T cells in the development of atherosclerotic lesion formation, WT or KLF10−/− CD4$^+$CD25$^-$ T cells were adoptively transferred into ApoE$^{-/-}$/scid/scid mice which lack functional T and B cells. Previous studies demonstrate markedly reduced atherosclerotic lesion formation in ApoE$^{-/-}$/scid/scid mice compared to ApoE$^{-/-}$ mice, an effect that can be rescued by adoptive transfer with CD4$^+$ T cells (Zhou et al., 2000; Zhou et al., 2006). As demonstrated in FIG. 5D, ApoE$^{-/-}$/scid/scid mice that received KLF10−/− CD4$^+$CD25$^-$ T cells accelerated atherosclerotic lesion formation by ~2-fold in comparison to WT CD4$^+$CD25$^-$ T cells and was associated with ~3-fold increased infiltration of CD4$^+$ T cells and Mac-3-positive macrophages after 4 weeks of high fat diet. Consistently, recipient ApoE−/−/scid/scid mice adoptively transferred with KLF10−/− CD4$^+$CD25$^-$ T cells had higher plasma levels of pro-inflammatory mediators MCP-1, SDF-1β, and MMP-9, whereas TGF-β1 plasma levels were lower (FIG. 5E). Importantly, there were no differences in plasma lipid profiles in recipient ApoE$^{-/-}$/scid/scid mice (Table 1).

TABLE 1

Mouse plasma lipid profiles.

| | Cholesterol (mg/dL) | Triglycerides (mg/dL) | HDL (mg/dL) | LDL (mg/dL) |
|---|---|---|---|---|
| WT | 930.3 ± 215 | 165.9 ± 12.5 | 92.9 ± 38.2 | 804 ± 236.3 |
| KLF10−/− | 713.5 ± 172.6 | 150.5 ± 24.1 | 57.6 ± 29.3 | 626 ± 324.8 |

All values vs. WT, P = NS. N = 4 WT and 6 KLF10−/− mice.

Finally, to assess if KLF10−/− CD4$^+$CD25$^-$ T cells also possessed impaired TGF-β signaling, cells were stimulated with anti-CD3 Abs and TGF-β1 for 1 hr and Western blot analyses were performed. As demonstrated in FIG. 5F, KLF10−/− CD4$^+$CD25$^-$ T cells possessed significantly reduced levels of phosphorylated Smad2, whereas there were no differences in the expression of Smad2, Smad7, or the TGF-β1 and II type receptors. These findings are consistent with a loss of cell intrinsic control of KLF10−/− CD4$^+$CD25$^-$ T cell activation. Taken together, these findings indicate that KLF10−/− CD4$^+$CD25$^-$ T cells are hyperactivated in response to TCR activation and in the pathophysiological context of vascular inflammation, effects that may be due to, in part, defective TGF-β signaling.

Discussion

This Example has shown that KLF10 is a novel regulator of CD4$^+$CD25$^-$ T cell activation, T regulatory cell differentiation, and T reg cell suppression function through distinct mechanisms. In support, KLF10 is a TGF-β1 responsive gene expressed highly in T regulatory cells and programs CD4$^+$CD25$^-$ T cell fate towards the CD4$^+$CD25$^+$ T regulatory cell lineage by targeted induction of the Foxp3 gene. Consistently, it was found that KLF10−/− mice have reduced numbers of peripheral CD4$^+$CD25$^+$ and CD4$^+$CD25$^+$Foxp3$^+$ T regulatory cells and KLF10-deficient CD4$^+$CD25$^-$ T cells have impaired Foxp3 expression in response to TGF-β1. Remarkably, KLF10-deficient T reg cells have reduced suppression function, independent of Foxp3 expression, due to decreased elaboration of TGF-β1 and defective TGF-β1/Smad signaling, an effect rescued by exogenous TGF-β1 administration to KLF10−/− T reg cells. Furthermore, cogent evidence was provided that supports a lack of cell-intrinsic control of T cell activation by TGF-β signaling in KLF10−/− CD4$^+$CD25$^-$ T cells whereby reduced Smad2 phosphorylation allows for enhanced elaboration of Th1 and Th2 cytokines in these cells and accelerated atherosclerosis in ApoE$^{-/-}$/scid/scid mice. A recent study by Venuprasad et al. identified that the E3 ubiquitin ligase Itch regulated the expression of KLF10 to modulate in vitro generated expression of Foxp3; in addition, they found that the in vitro generated, 'TGF-β converted' T regs from CD4$^+$CD25$^-$ T cells of KLF10−/− mice were unable to suppress airway inflammation (Venuprasad et al., 2008). Our findings extend these observations by delineating unique mechanisms in which KLF10 exacts its function in CD4$^+$CD25$^-$ T cells and T regulatory cells and highlight a critical role for KLF 10 in vascular inflammation.

KLFs in T Cells

Other Kruppel-like factors have been shown to play roles in various aspects of T cell differentiation, activation, and function (Bieker, 1996; Feinberg et al., 2004a). For example, KLF2 expression is induced upon differentiation of immature double-positive T cells (CD4$^+$CD8$^+$) to single positive T cells (CD4$^+$ or CD8$^+$) which circulate in the bloodstream. Indeed, gene-targeting studies revealed a role for this factor in programming the quiescent phenotype of single-positive T cells (Kuo et al., 1997). KLF2 also regulates T cell egress from the thymus and peripheral trafficking (Carlson et al., 2006). KLF13/RFLAT-1 (RANTES factor of late activated T lymphocytes) was originally identified by expression cloning by its ability to bind to a site and activate the RANTES promoter (Nikolcheva et al., 2002; Song et al., 1999). Recently, targeted disruption of KLF13 verified an important role for its regulation of RANTES expression and T cell survival (Zhou et al., 2007). Additional KLFs identified in T cells include KLF5 and KLF6, albeit their functional roles less well-defined. KLF5 was identified by virtue of its ability to bind to a GC-rich area of the TCR Dβ1 promoter, an effect raising the possibility that this factor may contribute to T cell lineage-specific TCRβ expression (Yang et al., 2003). Finally, overexpression of KLF6 induced iNOS gene expression and bound to the proximal iNOS promoter in response to a variety of pathophysiological stimuli such as hypoxia, heat shock, and serum starvation (Warke et al., 2003). The studies presented in this paper extend a participatory role of KLF proteins in both CD4$^+$CD25$^-$ T cells and T regulatory cells.

TGF-β1 and KLF10 Control of T Regulatory Cell Differentiation and Suppression Function Accumulating evidence supports a critical role for TGF-β1 and TGF-β signaling in the maintenance of self-tolerance and peripheral T regulatory cell development and function. TGF-β1−/− mice die within 4 weeks of birth due to a multifocal autoimmune disease characterized by severe multi-organ infiltration of autoreactive T cells and other leukocytes (Bommireddy et al., 2006). Phenotypic similarities in TGF-β1−/− mice and Foxp3-mutant mice elicited investigation of the role of TGF-β signaling to Foxp3 expression and generation of T regs. Indeed, TGF-β signaling induces Foxp3 and promotes peripheral conversion of naïve CD4$^+$CD25$^-$Foxp3$^-$ T cells into CD4$^+$CD25$^+$Foxp3$^+$ cells in vitro and in vivo (Bettelli et al., 2006; Carrier et al., 2007; Chen et al., 2003; Davidson et al., 2007; Fantini et al., 2004; Kretschmer et al., 2005; Wan and Flavell, 2005; Zheng et al., 2004). Moreover, TGF-β1−/− mice have impaired T reg suppression function as a result of defective TGF-β signaling (Bommireddy and Doetschman, 2007; Marie et al., 2005). Consistently, it was found that KLF10−/− mice also have reduced peripheral T regs, T reg suppression function, and TGF-β signaling. Because elaboration of TGF-β1 from KLF10−/− T regs was markedly decreased and exogenous TGF-β1 rescued the defect in KLF10−/− T reg suppression function, it is likely that the reduced Smad2-phosphorylation was a consequence of lower TGF-β1 levels rather than a downstream defect in Smad2 phosphorylation. In support, no difference was found in levels of TGF-β type I or II receptors, Smad2, or the inhibitory Smad, Smad7, in KLF10−/− and WT T regs. These findings also raise the provocative idea that KLF10 may serve as a positive auto-regulator of TGF-β signaling. Nevertheless, our findings do not exclude the possibility that defects may exist of unidentified Jun or MAP Kinases that, in theory, have the capacity to phosphorylate Smad2/3 in response to upstream signals (Brown et al., 1999; Engel et al., 1999). Finally, despite controlling for equal expression of Foxp3 in WT and KLF10−/− CD4$^+$CD25$^+$Foxp3$^+$ T regs, our studies reveal persistent impairment in suppression function in these KLF10−/− CD4$^+$CD25$^+$Foxp3$^+$ T regs, an effect that was also rescued by exogenous administration of TGF-β1. Indeed, KLF10−/− CD4$^+$CD25$^+$Foxp3$^+$ T regs elaborated lower TGF-β1 levels than WT CD4$^+$CD25$^+$Foxp3$^+$ T regs. Recent studies have identified Foxp3 transcription-factor dependent and independent molecules including TGF-β1, IL-10, CTLA4, granzyme B, perforin, heme oxygenase-1 (HO-1), cAMP, CD39, galectins, or IL-35, among others, as contributors to T reg suppression function (Tang and Bluestone, 2008; von Boehmer, 2005). Additional studies will be required to assess the relationship of TGF-β1, KLF10, and these other potential mediators in T reg suppression function.

Figure 5F:
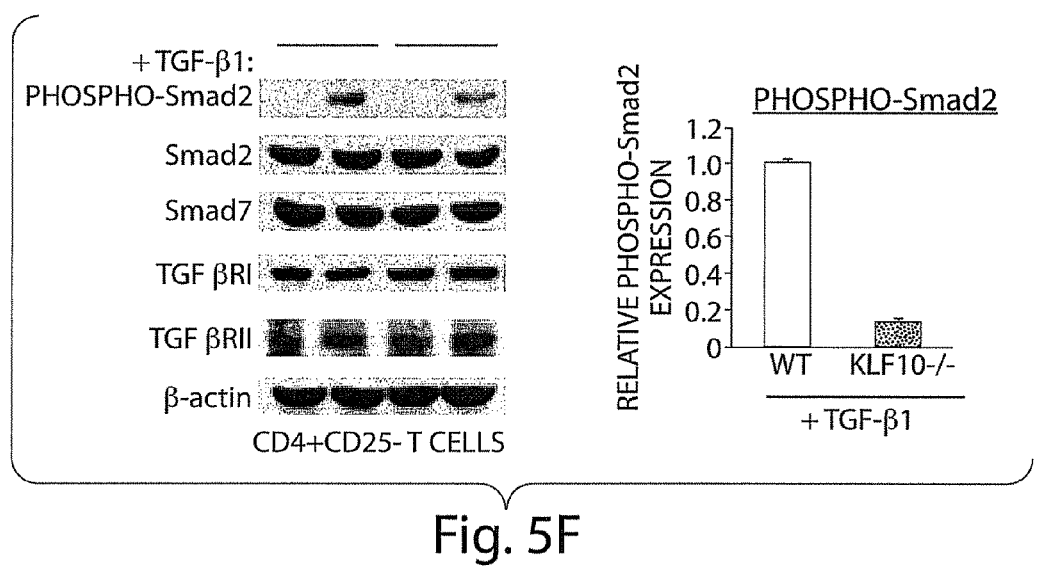
Figure 6A:
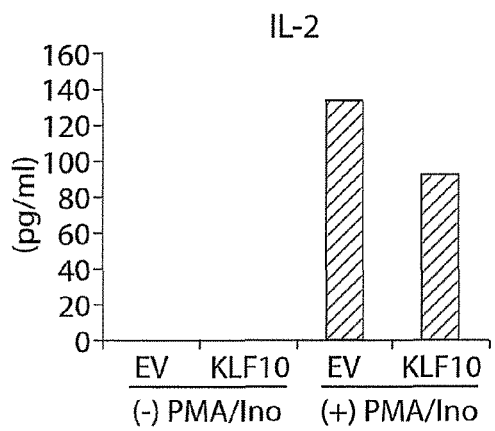
FIG. 6 depicts the effect of KLF10 overexpressing cells on cytokines/chemokines after stimulation with PMA/ionomycin as measured by ELISA including the cytokines/chemokines: (A) IL-2; (B) IFN-γ; (C) IFN-α; (D) IL-1β; (E) MIP-1α; (F) MIP-1β; (G) CD40L; and (H) RANTES.
Figure 6B:
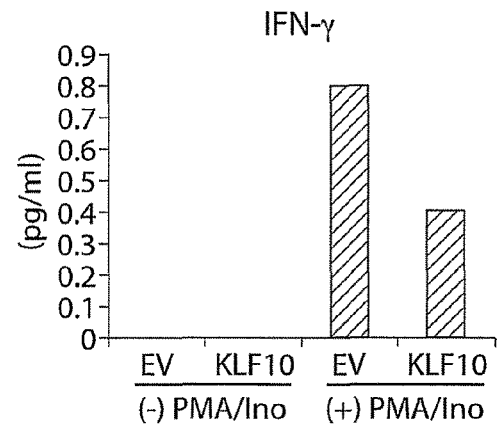
Figure 6C:
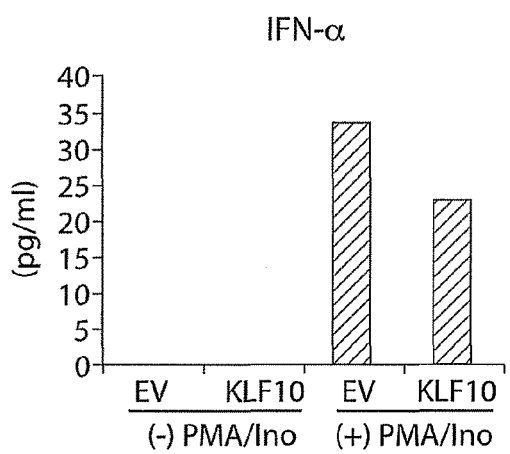
Figure 6D:
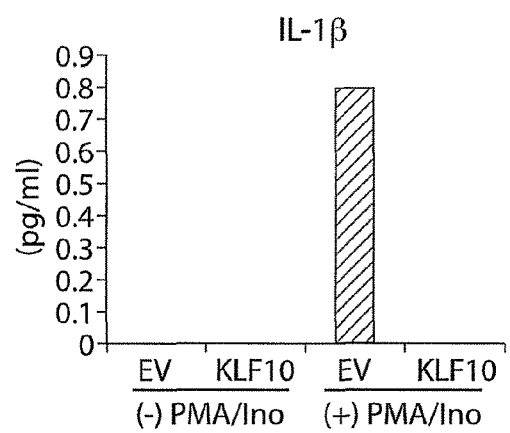
Figure 6E:
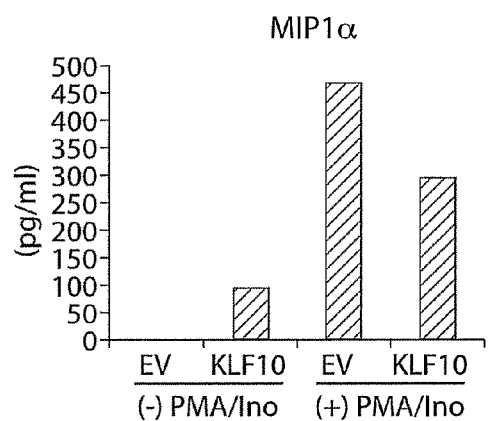
Figure 6F:
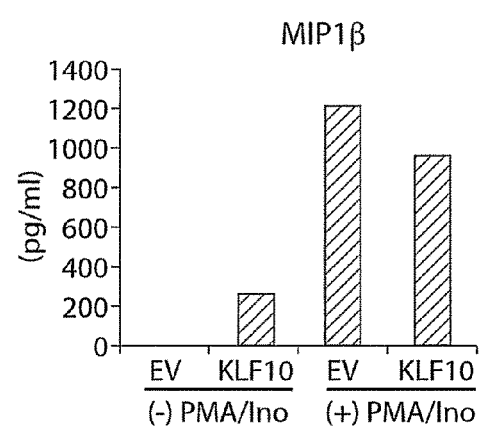
Figure 6G:
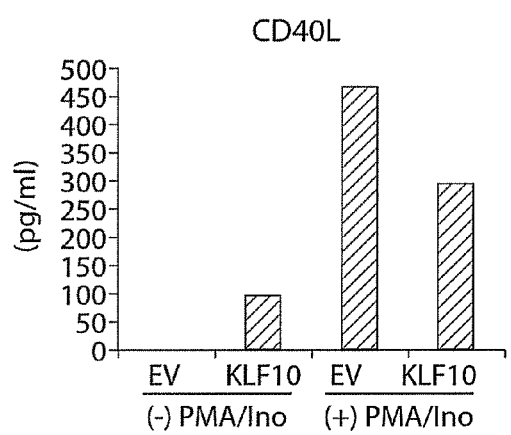
Figure 6H:
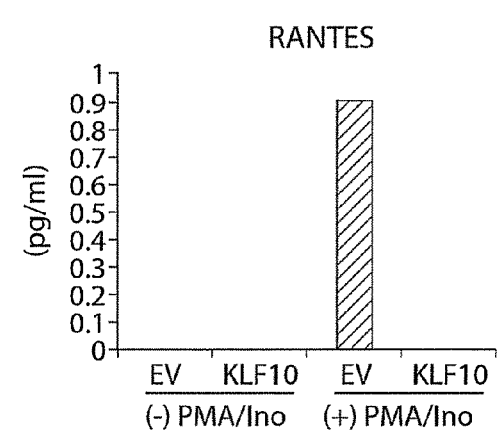
Figure 7A:
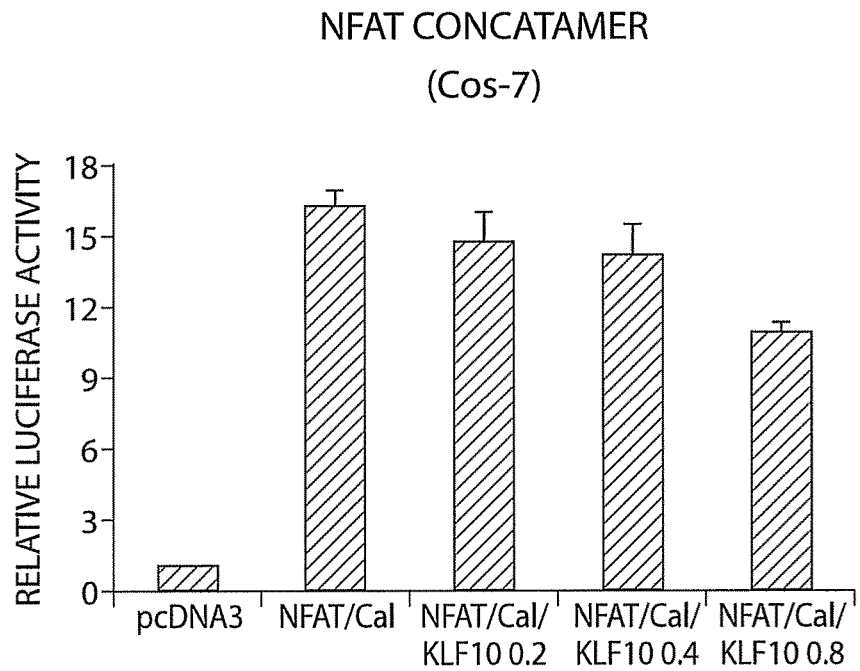
FIG. 7 depicts the effect of KLF10 in an NFAT concatamer assay and an IFNγ promoter assay: (A) KLF10 inhibits NFAT concatamer activity in Cos-7 cells; (B) KLF10 inhibits IFNγ promoter activity in Jurkat cells; (C) KLF10 inhibits NFAT concatamer activity in Cos-7 cells; and (D) KLF10 inhibits IFNγ promoter activity in Jurkat cells.
Figure 7B:
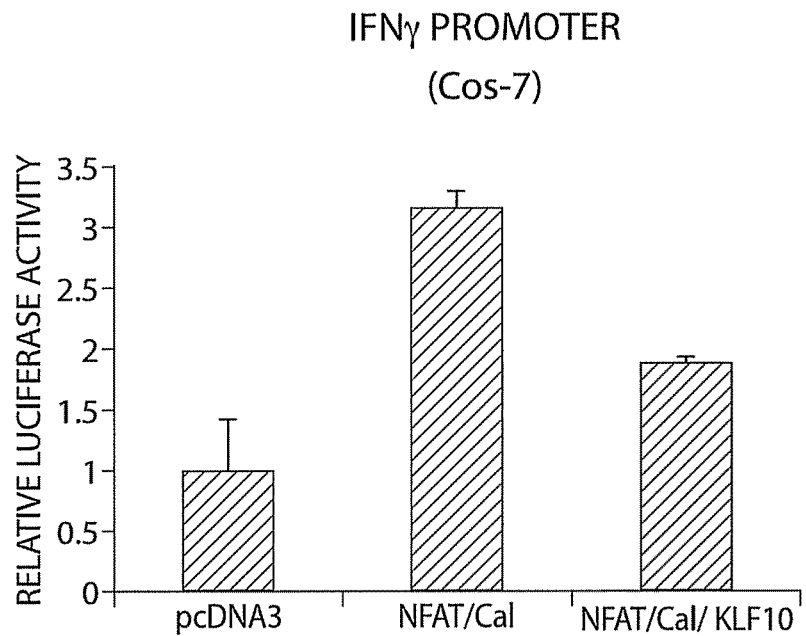
Figure 7C:
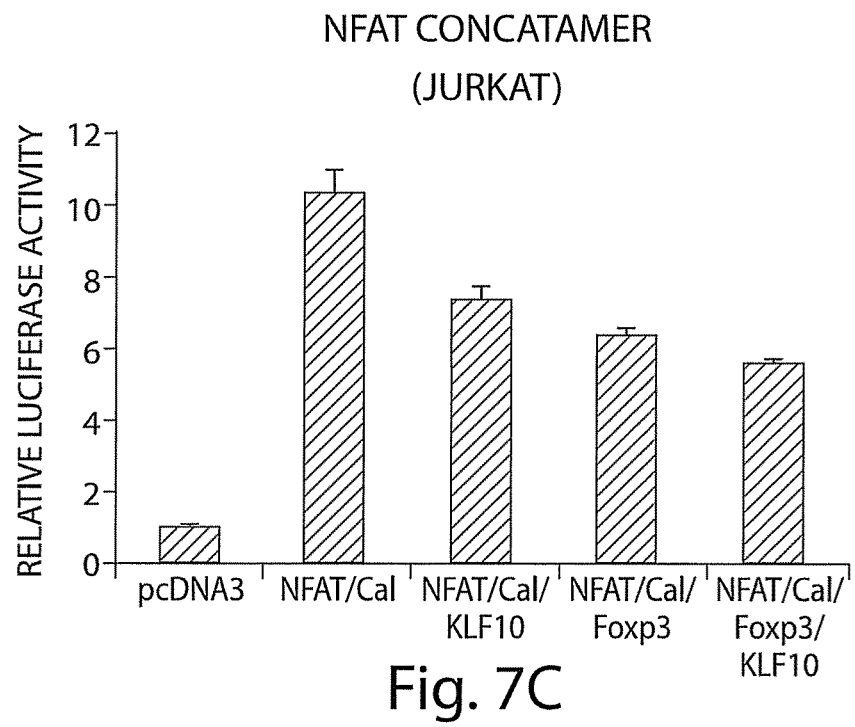
Figure 7D:
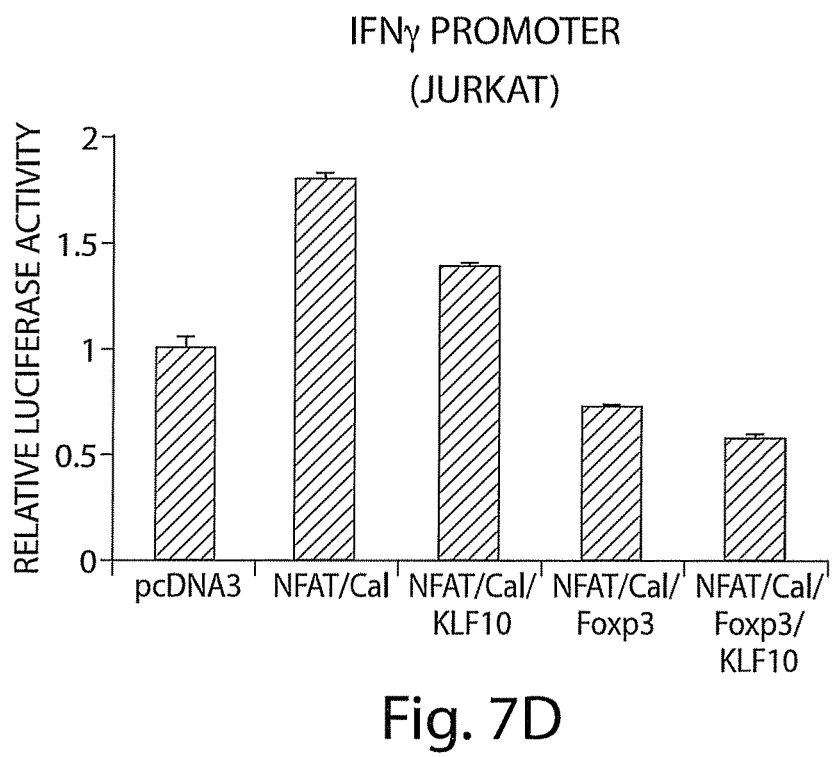
Figure 10A:
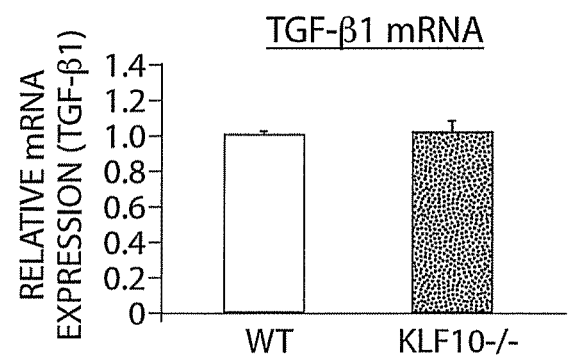
FIG. 10 depicts that KLF10−/− CD4+CD25− T cells have similar levels of TGF-β1 mRNA and secreted protein. WT or KLF10−/− CD4+CD25− T cells were stimulated with anti-CD3 Abs for 24 hrs and subjected to qPCR analyses (A) for TGF-β1 mRNA or culture supernatants were harvested and assessed by SearchLight Proteome Arrays/multiplex sandwich ELISA for TGF-β1 protein (B). Each sample was evaluated in triplicate and is representative of two independent experiments.
Figure 10B:
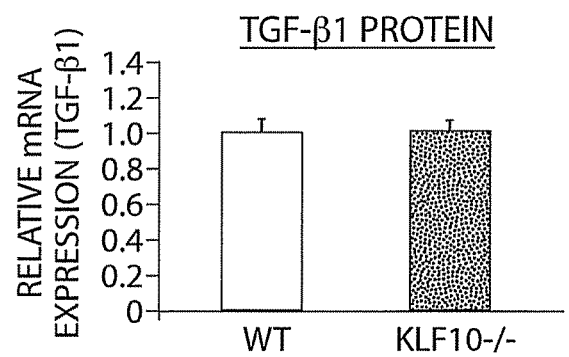

TGF-β1 and KLF10 Regulation of CD4$^+$CD25$^-$ T Cells—Balancing Effector Th1, Th2, and Th17 Pathways Accumulating studies have demonstrated that TGF-β1 inhibits both Th1 and Th2 cell differentiation pathways by inhibiting T-Bet and Gata3, Th1 and Th2 master transcription factors, respectively (Gorelik et al., 2000; Li and Flavell, 2008; Lin et al., 2005). While several direct and indirect mechanisms have been proposed, emerging evidence suggests that induction of Foxp3 may be a major determinant as a result of promoting T reg cell development, an effect that diminishes the abundance of cytokines conducive for differentiation into Th1 and Th2 pathways (Bommireddy and Doetschman, 2007; Kim and Rudensky, 2006; Zheng and Rudensky, 2007). Consistently, it was found that overexpression of KLF10 induced Foxp3 expression, whereas it repressed the expression of T-bet and Gata3 (FIG. 2C). Conversely, KLF10−/− CD4$^+$CD25$^-$ T cells had enhanced mRNA and secreted proteins for Th1 markers (e.g. IFN-γ, IL-2) and Th2 markers (e.g. IL-4, IL-5, and IL-13) in response to TCR activation (FIG. 5C). Moreover, in response to forced skewing along the Th1 and Th2 pathways, KLF10−/− CD4$^+$ T cells had markedly increased expression for Th1 markers, T-Bet and IFN-γ, and Th2 markers, Gata3 and IL-5, supporting the notion that these cells are 'hyperactivated' upon differentiation of these pathways (FIG. 3F). Similar to KLF10-deficient T regs, KLF10−/− CD4$^+$CD25$^-$ T cells had marked defects in TGF-β1 signaling and in the ability to be suppressed by co-cultured WT T regs. In contrast to KLF10−/− T regs, no differences were found in levels of TGF-β1 mRNA and secreted protein from TCR stimulated KLF10−/− CD4$^+$CD25$^-$ T cells in vitro (FIG. 10); however, TGF-β1 plasma levels were decreased in vivo after adoptive transfer of KLF10−/− CD4$^+$CD25$^-$ T cells in ApoE$^{-/-}$/scid/scid mice (FIG. 5E) and Smad2 phosphorylation was potently reduced in KLF10−/− CD4$^+$CD25$^-$ T cells (FIG. 5F). Collectively, these findings highlight that loss of cell-intrinsic control of T cell activation by TGF-β signaling is, in part, contributory to the CD4$^+$CD25$^-$ T cell phenotype from KLF10−/− mice. Indeed, TGF-βRII-deficient mice have reduced peripheral T regs, yet adoptive transfer of WT T regs is still unable to correct the phenotype of hyperactivated effector T cells observed in these mice (Li et al., 2006). Thus, in response to TGF-β, KLF10 maintains T cell tolerance by controlling both effector T cells and T reg cell responses.

TGF-β1/Smad Signaling in Vascular Inflammation

The composite anti-proliferative and anti-inflammatory effects of TGF-β1 on both the immune and nonimmune cellular constituents of the atherosclerotic lesion suggest an inhibitory role in atherogenesis. For example, blockade of TGF-β1 ligand or the TGF-β type II receptor accelerates the development of atherosclerotic lesion formation in ApoE$^{-/-}$ atherosclerotic-prone mice (Lutgens et al., 2002; Mallat et al., 2001). In patients, the serum concentration of active TGF-β1 is inversely correlated with the severity of atherosclerotic disease (Grainger et al., 1995). In the context of transplant-associated arteriosclerosis (TxAA), cardiac allografts from recipient mice heterozygous for TGF-β1 displayed a marked increase in TxAA in comparison to wild-type controls (Koglin et al., 1998). It was previously demonstrated that allografts from Smad3-deficient mice develop robust leukocyte infiltration and accelerated vascular arteriopathy (Feinberg et al., 2004b). Our studies here demonstrate that KLF10-deficient CD4$^+$CD25$^-$ T cells have impaired TGF-β signaling with hyperactived T cell cytokine profiles and accelerate atherosclerotic lesion formation in ApoE$^{-/-}$/scid/scid mice, effects consistent with the premise that defective TGF-β signaling promotes atherogenesis. To our knowledge, KLF10 is the first KLF family member identified to regulate T-cell mediated atherosclerotic lesion formation in vivo. It will be of interest to explore if KLFs that are antithetically expressed in T reg. cells such as KLF4 or KLF5 (FIG. 1B) may also have a participatory role in the immune response and atherosclerotic lesion formation.

Materials and Methods

Detailed materials and methods are available in the Supplementary Information at The EMBO Journal Online (http://www.embojournal.org), all of which are incorporated herein by reference in their entireties.

Supplementary Materials and Methods

Cell Culture And Reagents

Primary CD4$^+$CD25$^-$ and CD4$^+$CD25$^+$ were isolated from mouse spleens by using magnetic-based isolation kit (Miltenyi Biotech), followed by FACS sorting (>99% pure), and grown in RPMI 1640 medium (ATCC) supplemented with 10% FBS, 0.02 mM beta-mercaptoethanol. Jurkat cells were obtained from American Type Culture Collection (ATCC) and cultured as recommended.

Mice

KLF10−/− mice, originally from the laboratory of Dr. Thomas Spelsberg (Mayo Clinic), and ApoE−/−/scid/scid mice from the laboratory of Dr. Goran Hansson (Korolinska Institute, Sweden) have been described (refs). Mouse genotypes were determined by PCR. Mice 8-12 week of age were used for most of experiments.

In Vitro Suppression Assays $CD4^+CD25^-$ and $CD4^+CD25^+$ T cell populations were isolated from WT and KLF10−/− mice spleens or mesenteric lymph nodes. $CD4^+CD25^-$ responder cells ($5\times10^4$) were co-cultured with various ratios of $CD4^+CD25^+$ T cells as indicated in the presence of 1 ug/ml anti-CD3 (clone 2C11) in 96-well microplate plates for 72 hours. Cultures were pulsed with 1 μCi [$^3$H]thymidine per well for the last 18 hours. After the 72 h incubation, the cultures were harvested and [$^3$H]thymidine incorporation was measured by scintillation counting.

Northern and Western Analyses

Total RNA was isolated from cultured cells using Trizol methods as previously described (Feinberg et al., 2007). Cellular protein extraction and Western blot analyses were performed as described (Feinberg et al., 2007).

Retroviral Transduction

For retroviral studies, the indicated cDNA (mouse KLF10) was cloned into the retroviral vector GFP-RV (gift from K Murphy) and retrovirus generated as described (Feinberg et al., 2007). For retroviral infection of Jurkat EcoR and primary $CD4^+CD25^-$ cells, cells were cultured in 6-well plates at $2\times10^6$ per well, infected with empty vector (EV) and KLF10 retroviral supernatant generated from phoenix cells, and centrifuged at 1800 rpm for 45 min. Retroviral supernatant and culture medium (10% FCS/DMEM+8 μg/ml Polybrene) were mixed at a 1:1 ratio. The next day, cell media were changed with fresh cell culture RPMI medium. GFP positive cells were then sorted 48 h after infection.

ELISAs Using Searchlight Multiplex Protein Arrays

Primary $CD4^+CD25^-$, Jurkat EcoR cells were retrovirally infected with EV or KLF10 for 48 hrs, followed by stimulation with PMA (20 ng/ml)/ionomycin (3.5 μg/ml) for 6 hrs. The supernatants were collected for ELISA analysis using Searchlight Multiplex protein arrays (Pierce). Cell culture media from $CD4^+CD25^-$, $CD4^+CD25^+$, and $CD4^+CD25^+$ Foxp3$^+$ T cells and the plasma from adoptive transferred ApoE$^{-/-}$/scid/scid mice were also collected for ELISA analyses.

Atherosclerosis Induction by Adoptive Transfer of $CD4^+CD25^-$ T Cells in ApoE$^{-/-}$/scid/scid Mice.

Wild-type and KLF10−/− $CD4^+CD25^-$ cells were isolated and injected into 8-10 week ApoE/Scid mice by retro-orbital vein. Recipient mice were provided with a high fat diet after injection for 4 weeks. Mice were sacrificed and plasma samples were collected for ELISA analysis and cholesterol measurement. Mouse hearts were embedded in Optimal Cutting Temperature (OCT) compound and the sections were stained with Oil red O, Mac-3, and CD4 for lesion characterization and macrophage, T cell infiltration.

Quantitative Real-time PCR.

Total RNA from purified $CD4^+CD25^-$ and $CD4^+CD25^+$ cells was isolated using Trizol reagent (Invitrogen). The real time PCR was performed in triplicates with Brilliant SYBR green mix using the Mx3000P Real-Time PCR system (Stratagene). β-actin was used to normalize the samples. Primers sequences are listed in Table 2.

TABLE 2

| | qPCR primer sequences: | |
|---|---|---|
| | Forward (5'-3') | Reverse (5'-3') |
| Foxp3 | CCCATCCCCAGGAGTCTTG (SEQ ID NO: 1) | ACCATGACTAGGGGCACTGTA (SEQ ID NO: 2) |
| KLF10 | TTCTCTCCAGCAAGCTTCGGA (SEQ ID NO: 3) | TCACTCTGCTCAGCTTTGTCCC (SEQ ID NO: 4) |
| KLF2 | GGACCTAAACAACGTGTTGGA (SEQ ID NO: 5) | CTCCGGGTAGTAGAAGGCAG (SEQ ID NO: 6) |
| KLF4 | TGATGGTGCTTGGTGAGTTG (SEQ ID NO: 7) | TTGCACATCTGAAACCACAG (SEQ ID NO: 8) |
| KLF5 | TTCCAAACTGGCGATTCACAA (SEQ ID NO: 9) | ATTAACTGGCAGAGTGGCAGGTAA (SEQ ID NO: 10) |
| T-bet | CCTGTTGTGGTCCAAGTTCAAC (SEQ ID NO: 11) | CACAAACATCCTGTAATGGCTTGT (SEQ ID NO: 12) |
| GATA3 | GCCATGGGTTAGAGAGGCAG (SEQ ID NO: 13) | TTGGAGACTCCTCACGCATGT (SEQ ID NO: 14) |
| IL-2 | GTGCTCCTTGTCAACAGCG (SEQ ID NO: 15) | GGGGAGTTTCAGGTTCCTGTA (SEQ ID NO: 16) |
| IFNγ | GAACTGGCAAAAGGATGGTGA (SEQ ID NO: 17) | TGTGGGTTGTTGACCTCAAAC (SEQ ID NO: 18) |
| TGFβ1 | ATCCTGTCCAAACTAAGGCTCG (SEQ ID NO: 19) | ACCTCTTTAGCATAGTAGTCCGC (SEQ ID NO: 20) |
| β-Actin | GAAATCGTGCGTGACATCAAAG (SEQ ID NO: 21) | TGTAGTTTCATGGATGCCACAG (SEQ ID NO: 22) |
| IL-4 | GGTCTCAACCCCCAGCTAGT (SEQ ID NO: 23) | GCCGATGATCTCTCTCAAGTGAT (SEQ ID NO: 24) |
| IL-17 | TTTAACTCCCTTGGCGCAAAA (SEQ ID NO: 25) | CTTTCCCTCCGCATTGACAC (SEQ ID NO: 26) |

Flow Cytometric Analysis and Cell Sorting.

For FACS analysis, APC, PE, or FITC-conjugated antibodies specific for CD4, CD25, and Foxp3 were used to label CD4+CD25−, CD4+CD25+, and CD4+CD25+FOXP3+ T cells as described by the manufacturer's protocol (eBioscience). FACS analysis was performed on a FACSCalibur flow cytometer and analyzed with CellQuest (Becton Dickison, Franklin Lakes, N.J., USA). Sorted CD4+CD25+ and CD4+CD25+Foxp3+ cells were used in suppression assays. Retrovirally infected CD4$^+$CD25$^-$ cells with EV and KLF10 were also sorted for GFP-positive cells and used in suppression assays. Cell culture media were collected for ELISA analysis.

Antibodies.

Polyclonal KLF10 antibody was used as described (Subramaniam et al., 1995). Antibodies to Smad2 (#3103), phosphorylated-Smad2 (#3108), β-actin (#4967L) were from Cell Signaling. Smad7 (42-0400) was obtained from Zymed Laboratories. TGF-βR1 (ab31013) was obtained from Abcam. IgG (sc-2025) and TGF-βRII (sc-400) antibodies were from Santa Cruz Biotechnology. Allophycocyanin-labeled anti-CD4 (RM4-5), phycoerythrin-labeled anti-CD25 (pc61.5), and FITC-labeled anti-Foxp3 (FJK-16a), and Foxp3 (eBio7979) were purchased from eBioscience.

SiRNA by Amaxa Nucleofection.

To knockdown KLF10 in CD4$^+$CD25$^-$ cells, 5×10$^6$ cells were transfected with 100 nM siKLF10 (Dharmacon) or non-specific control using Amaxa nucleofection (program X-001) for 48 hrs. Cells were then treated with or without TGF-β1 (1 ng/ml) and harvested for mRNA.

Chromatin Immunoprecipitation (ChIP) Assay.

ChIP assay was performed using the kit from Upstate-Millipore according to manufacturer's protocol. In brief, CD4$^+$CD25$^-$ (2.5×10$^6$) cells were isolated from wild-type mice and stimulated with anti-CD3 (3 µg/ml) for 24 h, followed by treatment with or without TGF-β1 (1 ng/ml) for 6 h. Cells were then fixed with 1% formaldehyde and chromatin was fragmented by sonication. Sheared chromatin was pre-cleared with salmon sperm DNA/protein A agarose and immunoprecipitated with 5 µg control IgG or anti-KLF10 antibody at 4° C. for overnight. The antibody/histone complex was collected by the incubation with salmon salmon sperm DNA/protein A agarose at 4° C. for 2 h. To reverse the histone-DNA crosslinks, precipitates were heated at 65° C. for overnight. DNA was recovered and purified by phenol/chloroform extraction and ethanol precipitation. PCR primers for the Foxp3 promoter were 5'-GGACGCTGCT-GAGTGGAAGAG-3' (SEQ ID NO: 27) and 5'-AAGGCAGGGAGCGGAGAC-3' (SEQ ID NO: 28) . ChIP assay was also verified by qPCR. The primers used for QPCR were: forward 5' GTGGTGAGGGGAAGAAATC 3' (SEQ ID NO: 29); reverse 5' CGTGGAAGCCGCAGAC-CTC 3' (SEQ ID NO: 30). Data were presented as fold-change versus DNA input.

Transient Transfection Reporter Assays.

CD4$^+$CD25$^-$ or CD4$^+$CD25$^+$ T cells (5×10$^6$ each) were co-transfected with the Foxp3 promoter (−348/+176) (kindly provided by Schmidt-Weber, C. Swiss Institute of Allergy and Asthma Research, (Mantel et al., 2006)), pcDNA3 or KLF10 in the presence or absence of TGFβ1 using Amaxa Nucleofection (program X-001) for 24 hours as described by the manufacturer's protocol. In brief, 4 µg of total plasmid DNA was used in the experiments. Luciferase activity was normalized to β-galactosidase activity by cotransfecting the pCMV-β-gal plasmid (0.5 µg) in all experiments. All transfections were performed in triplicate from at least independent experiments. Site-directed mutagenesis (Stratagene) was performed to generate the Foxp3 promoter with mutant KLF site. The PCR primer sequences used to generate this mutant Foxp3 promoter were: forward 5'-AAACTATGAGAAC-CTTTTCGAATTCCGTGATTATCAGCGC-3' (SEQ ID NO: 31); reverse 5'-GCGCTGATAATCACGGAATTC-GAAAAGGTTCTCATAGTT-3' (SEQ ID NO: 32).

Th1 and Th2 Cell Skewing Experiments.

CD4$^+$ T cells were purified using anti-CD4 beads (Miltenyi) and further sorted into naïve CD4$^+$CD25$^-$CD62L$^{hi}$ T cells. Th1 and Th2 cell differentiation was performed as described (Bettelli et al., 2006). Cells were stimulated with anti-CD3 and anti-CD28 Abs for 2-3 days in the presence of recombinant IL-12 (10 ng/mL, R&D Systems) and neutralizing antibodies to IL-4 (10 µg/mL, 11B11, R&D Systems) for Th1 cell differentiation and in the presence of recombinant IL-4 (10 ng/mL, R&D Systems) and neutralizing antibodies to IFN-γ (10 µg/mL, XMG1.2, R&D Systems) for Th2 cell differentiation. Cholesterol Measurements. The plasma samples from adoptive transferred ApoE$^{-/-}$/scid/scid mice were used to measure total cholesterol (C7510-120), triglycerides (T7532-120), and HDL cholesterol (H7511-60) levels by the kits from Pointe Scientific Inc. LDL cholesterol level was calculated based on the values of total cholesterol, triglycerides, and HDL.

Statistical Analyses.

Values are expressed as means+SD. Differences between values were examined using the two-tailed Student's t-test and were considered significant at $p<0.05$.

Example 2

KLF10 Inhibits T Cell Activation in Two Pathways (TGF-β Signaling Pathway and the TCR Signaling Pathway)

Magnetic microbead separation was performed to isolate CD4+CD25− and CD4+CD25+ fractions from mice (purity>95%). Real-Time PCR experiments on the isolated fractions identified that among a panel of KLFs, KLF10 mRNA was robustly expressed (~6-fold) in naïve CD4+CD25+ T regulatory cells in comparison to CD4+CD25− cells (FIG. 1A). Because TGF-β1 induces CD4+CD25+ T regulatory cells from CD4+CD25− precursors, the kinetics of KLF10 mRNA was examined in CD4+CD25− cells in response to TGF-β1 (10 ng/ml) at 1, 6, and 24 hrs. KLF10 mRNA was markedly induced in CD4+CD25− by ~23-fold at 1 hr, ~27-fold at 6 hr, and ~7.5 fold at 24 hrs of TGF-β1 treatment (FIG. 1C). Remarkably, TGF-β1 induced the expression pattern of the T regulatory marker, Foxp3, in an analogous pattern as KLF10 (FIG. 1C). TGF-β1 also induced expression of KLF10 after 1 hr in the Jurkat T cell line (FIG. 1D-1G). Retroviral overexpression of KLF10 alone in Jurkat cells conferred the cell surface characteristics of a T regulatory cell (CD25, GITR, CD45, and intracellular Foxp3) (FIG. 2). In addition, knockdown of KLF10 by KLF10-targeted siRNA markedly reduced expression of Foxp3 in primary T cells (FIGS. 3A, 3B). Functionally, KLF10 overexpressing cells blocked the elaboration of a variety of cytokines/chemokines after stimulation with PMA (20 ng/ml)/ionomycin (3.5 ug/ml) for 6 hrs including TNF-α, IL-2, IFN-γ, IFN-α, IL-1β, MIP-1α, MIP-1β, CD40L, and RANTES as measured by ELISA (FIGS. 6A-6H). In addition, KLF10 expression is decreased in spleens and T cells from atherosclerotic-prone ApoE-deficient mice. Thus the results indicate that KLF10 expression participates in a step in the TGF-β signaling pathway. The ability of KLF10 to act as a transcription factor results in the expression of Foxp3 and possibly other TGF-β regulated genes.

Figure 8A:
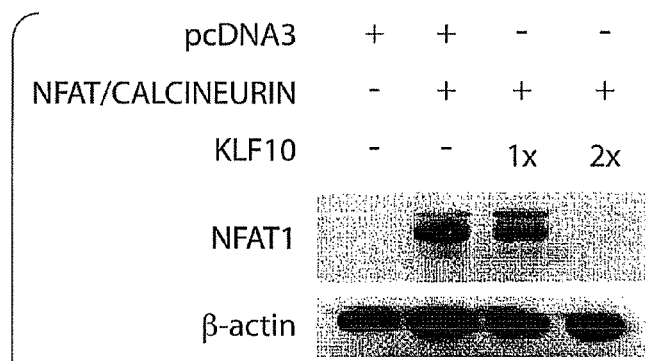
FIG. 8 depicts KLF10 regulation of NFAT1: (A) KLF10 inhibits NFAT1 expression; and (B) KLF10 inhibits NFAT DNA-protein binding to the IFNγ promoter.
Figure 8B:
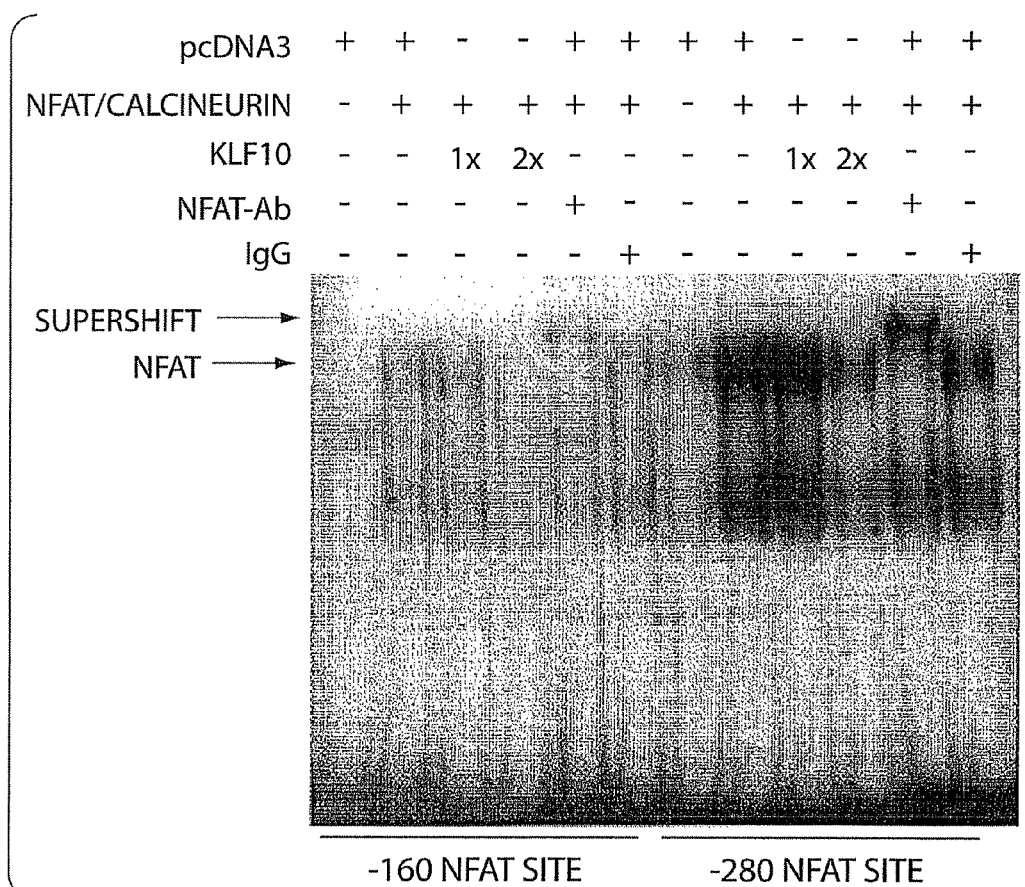

In addition to regulating Foxp3, data indicate that KLF10 inhibits T cell activation by negatively regulating NFAT, a potent transcriptional activator in T cells mediated by TCR signaling. Reporter gene experiments show that KLF10 can inhibit constitutively active NFAT (FIG. 7). Additionally, treatment with KLF10 correlates with inhibition of NFAT1 expression (FIG. 8A). Treatment with KLF10 also interferes with NFAT DNA-protein binding to the IFN-γ promoter (FIG. 8B). Thus the results of the experiments indicate that KLF10 negatively regulates the TCR signaling pathway by interfering with NFAT. The data suggest that KLF10 negatively regulates NFAT at least by reducing its expression, by interfering with its binding to its DNA binding site thereby preventing it from activating NFAT target genes (e.g., IFN-γ), or a combination of the two mechanisms. Therefore KLF10 functions in two pathways that inhibit T cell activation, including the TGF-β signaling pathway and the TCR signaling pathway.

KLF10 is the first member of this family to be identified as an important regulator of T regulatory cells. These studies may allow for novel therapeutic strategies for treatment of chronic inflammatory states such as atherosclerosis.

It will be appreciated that a beneficial agent including a therapeutically effective amount of a KLF10 polypeptide or fragment thereof can be delivered to a treatment site within a patient in a variety of ways. For example, such a beneficial agent can be delivered to a treatment location in a patient's vasculature on any of a variety of stents, such as those described in U.S. Pat. Nos. 6,106,548, 6,056,776, 6,547,817, 6,443,982, 5,356,423, 5,540,712, 5,716,393, 6,423,084, 5,913,895, 5,855,600, 5,938,697, 5,817,152, 5,707,386 and 6,558,415. Each of these patents is incorporated by reference herein in its entirety. These stents can be delivered using catheters described, for example, in U.S. Pat. Nos. 6,575,993, 5,906,619, 6,019,778, and 5,728,067. Each of these patents is incorporated by reference herein in its entirety.

REFERENCES

Ait-Oufella et al. Natural regulatory T cells control the development of atherosclerosis in mice. *Nat Med.* 2006 February;12(2):178-80.

Bettelli, E., Carrier, Y., Gao, W., Korn, T., Strom, T. B., Oukka, M., Weiner, H. L. and Kuchroo, V. K. (2006) Reciprocal developmental pathways for the generation of pathogenic effector TH17 and regulatory T cells.[see comment]. *Nature*, 441, 235-238.

Feinberg, M. W., Wara, A. K., Cao, Z., Lebedeva, M. A., Rosenbauer, F., Iwasaki, H., Hirai, H., Katz, J. P., Haspel, R. L., Gray, S., Akashi, K., Segre, J., Kaestner, K. H., Tenen, D. G. and Jain, M. K. (2007) The Kruppel-like factor KLF4 is a critical regulator of monocyte differentiation. *EMBO Journal*, 26, 4138-4148.

Mallat et al. Induction of a regulatory T cell type 1 response reduces the development of atherosclerosis in apolipoprotein E-knockout mice. *Circulation.* 2003 Sep. 9;108(10):1232-7.

Mantel, P. Y., Ouaked, N., Ruckert, B., Karagiannidis, C., Welz, R., Blaser, K. and Schmidt-Weber, C. B. (2006) Molecular mechanisms underlying FOXP3 induction in human T cells. *Journal of Immunology*, 176, 3593-3602.

Marie et al. TGF-β1 maintains suppressor function and Foxp3 expression in CD4+CD25+ regulatory T cells. *J Exp Med.* 2005 Apr. 4;201(7):1061-7.

Subramaniam, M., Harris, S. A., Oursler, M. J., Rasmussen, K., Riggs, B. L. and Spelsberg, T. C. (1995) Identification of a novel TGF-beta-regulated gene encoding a putative zinc finger protein in human osteoblasts. *Nucleic Acids Research*, 23, 4907-4912.

Bennett, C. L., Christie, J., Ramsdell, F., Brunkow, M. E., Ferguson, P. J., Whitesell, L., Kelly, T. E., Saulsbury, F. T., Chance, P. F. and Ochs, H. D. (2001) The immune dysregulation, polyendocrinopathy, enteropathy, X-linked syndrome (IPEX) is caused by mutations of FOXP3. *Nature Genetics*, 27, 20-21.

Bettelli, E., Carrier, Y., Gao, W., Korn, T., Strom, T. B., Oukka, M., Weiner, H. L. and Kuchroo, V. K. (2006) Reciprocal developmental pathways for the generation of pathogenic effector TH17 and regulatory T cells.[see comment]. *Nature*, 441, 235-238.

Bieker, J. J. (1996) Isolation, genomic structure, and expression of human erythroid Kruppel-like factor (EKLF). *DNA & Cell Biology*, 15, 347-352.

Bluestone, J. A. and Tang, Q. (2005) How do CD4+CD25+ regulatory T cells control autoimmunity? *Current Opinion in Immunology*, 17, 638-642.

Bommireddy, R. and Doetschman, T. (2007) TGFbeta1 and Treg cells: alliance for tolerance. *Trends in Molecular Medicine*, 13, 492-501.

Bommireddy, R., Pathak, L. J., Martin, J., Ormsby, I., Engle, S. J., Boivin, G. P., Babcock, G. F., Eriksson, A. U., Singh, R. R. and Doetschman, T. (2006) Self-antigen recognition by TGF beta1-deficient T cells causes their activation and systemic inflammation. *Laboratory Investigation*, 86, 1008-1019.

Brown, J. D., DiChiara, M. R., Anderson, K. R., Gimbrone, M. A., Jr. and Topper, J. N. (1999) MEKK-1, a component of the stress (stress-activated protein kinase/c-Jun N-terminal kinase) pathway, can selectively activate Smad2-mediated transcriptional activation in endothelial cells. *J Biol Chem*, 274, 8797-8805.

Carlson, C. M., Endrizzi, B. T., Wu, J., Ding, X., Weinreich, M. A., Walsh, E. R., Wani, M. A., Lingrel, J. B., Hogquist, K. A. and Jameson, S. C. (2006) Kruppel-like factor 2 regulates thymocyte and T-cell migration. *Nature*, 442, 299-302.

Carrier, Y., Yuan, J., Kuchroo, V. K. and Weiner, H. L. (2007) Th3 cells in peripheral tolerance. I. Induction of Foxp3-positive regulatory T cells by Th3 cells derived from TGF-beta T cell-transgenic mice. *Journal of Immunology*, 178, 179-185.

Chatila, T. A., Blaeser, F., Ho, N., Lederman, H. M., Voulgaropoulos, C., Helms, C. and Bowcock, A. M. (2000) JM2, encoding a fork head-related protein, is mutated in X-linked autoimmunity-allergic disregulation syndrome. [see comment]. *Journal of Clinical Investigation*, 106, R75-81.

Chen, W., Jin, W., Hardegen, N., Lei, K. J., Li, L., Marinos, N., McGrady, G. and Wahl, S. M. (2003) Conversion of peripheral CD4+CD25− naive T cells to CD4+CD25+ regulatory T cells by TGF-beta induction of transcription factor Foxp3. *Journal of Experimental Medicine*, 198, 1875-1886.

Davidson, T. S., DiPaolo, R. J., Andersson, J. and Shevach, E. M. (2007) Cutting Edge: IL-2 is essential for TGF-beta-mediated induction of Foxp3+ T regulatory cells. *Journal of Immunology*, 178, 4022-4026.

Engel, M. E., McDonnell, M. A., Law, B. K. and Moses, H. L. (1999) Interdependent SMAD and JNK signaling in transforming growth factor-beta-mediated transcription. *Journal of Biological Chemistry*, 274, 37413-37420.

Fantini, M. C., Becker, C., Monteleone, G., Pallone, F., Galle, P. R. and Neurath, M. F. (2004) Cutting edge: TGF-beta induces a regulatory phenotype in CD4+CD25− T cells through Foxp3 induction and down-regulation of Smad7. *Journal of Immunology*, 172, 5149-5153.

Feinberg, M. W. and Jain, M. K. (2005) Role of transforming growth factor-beta1/Smads in regulating vascular inflammation and atherogenesis. *Panminerva Medica*, 47, 169-186.

Feinberg, M. W., Lin, Z., Fisch, S. and Jain, M. K. (2004a) An emerging role for Kruppel-like factors in vascular biology. *Trends Cardiovasc Med*, 14, 241-246.

Feinberg, M. W., Shimizu, K., Lebedeva, M., Haspel, R., Takayama, K., Chen, Z., Frederick, J. P., Wang, X. F., Simon, D. I., Libby, P., Mitchell, R. N. and Jain, M. K. (2004b) Essential role for Smad3 in regulating MCP-1 expression and vascular inflammation. *Circ Res*, 94, 601-608.

Feinberg, M. W., Wara, A. K., Cao, Z., Lebedeva, M. A., Rosenbauer, F., Iwasaki, H., Hirai, H., Katz, J. P., Haspel, R. L., Gray, S., Akashi, K., Segre, J., Kaestner, K. H., Tenen, D. G. and Jain, M. K. (2007) The Kruppel-like factor KLF4 is a critical regulator of monocyte differentiation. *EMBO Journal*, 26, 4138-4148.

Fontenot, J. D. and Rudensky, A. Y. (2005) A well adapted regulatory contrivance: regulatory T cell development and the forkhead family transcription factor Foxp3. *Nature Immunology*, 6, 331-337.

Fu, S., Zhang, N., Yopp, A. C., Chen, D., Mao, M., Zhang, H., Ding, Y. and Bromberg, J. S. (2004) TGF-beta induces Foxp3+ T-regulatory cells from CD4+CD25− precursors. *American Journal of Transplantation*, 4, 1614-1627.

Gorelik, L., Fields, P. E. and Flavell, R. A. (2000) Cutting edge: TGF-beta inhibits Th type 2 development through inhibition of GATA-3 expression. *Journal of Immunology*, 165, 4773-4777.

Grainger, D. J., Kemp, P. R., Metcalfe, J. C., Liu, A. C., Lawn, R. M., Williams, N. R., Grace, A. A., Schofield, P. M. and Chauhan, A. (1995) The serum concentration of active transforming growth factor-beta is severely depressed in advanced atherosclerosis [see comments]. *Nature Medicine*, 1, 74-79.

Hansson, G. K. and Libby, P. (2006) The immune response in atherosclerosis: a double-edged sword. *Nature Reviews. Immunology*, 6, 508-519.

Kim, J. M. and Rudensky, A. (2006) The role of the transcription factor Foxp3 in the development of regulatory T cells. *Immunological Reviews*, 212, 86-98.

Koglin, J., Glysing-Jensen, T., Raisanen-Sokolowski, A. and Russell, M. E. (1998) Immune sources of transforming growth factor-beta1 reduce transplant arteriosclerosis: insight derived from a knockout mouse model. *Circulation Research*, 83, 652-660.

Kretschmer, K., Apostolou, I., Hawiger, D., Khazaie, K., Nussenzweig, M. C. and von Boehmer, H. (2005) Inducing and expanding regulatory T cell populations by foreign antigen. *Nature Immunology*, 6, 1219-1227.

Kuo, C. T., Veselits, M. L. and Leiden, J. M. (1997) LKLF: A transcriptional regulator of single-positive T cell quiescence and survival [see comments]. *Science*, 277, 1986-1990.

Li, M. O. and Flavell, R. A. (2008) TGF-beta: a master of all T cell trades. *Cell*, 134, 392-404.

Li, M. O., Sanjabi, S. and Flavell, R. A. (2006) Transforming growth factor-beta controls development, homeostasis, and tolerance of T cells by regulatory T cell-dependent and -independent mechanisms.[see comment]. *Immunity*, 25, 455-471.

Lin, J. T., Martin, S. L., Xia, L. and Gorham, J. D. (2005) TGF-beta 1 uses distinct mechanisms to inhibit IFN-gamma expression in CD4+ T cells at priming and at recall: differential involvement of Stat4 and T-bet. *Journal of Immunology*, 174, 5950-5958.

Lutgens, E., Gijbels, M., Smook, M., Heeringa, P., Gotwals, P., Koteliansky, V. and Daemen, M. (2002) Transforming growth factor-b mediates balance between inflammation and fibrosis during plaque progression. *Arteriosclerosis, Thrombosis & Vascular Biology*, 22, 975-982.

Mallat, Z., Gojova, A., Marchiol-Fournigault, C., Esposito, B., Kamate, C., Merval, R., Fradelizi, D. and Tedgui, A. (2001) Inhibition of transforming growth factor-beta signaling accelerates atherosclerosis and induces an unstable plaque phenotype in mice.[comment]. *Circulation Research*, 89, 930-934.

Marie, J. C., Letterio, J. J., Gavin, M. and Rudensky, A. Y. (2005) TGF-beta1 maintains suppressor function and Foxp3 expression in CD4+CD25+ regulatory T cells. *Journal of Experimental Medicine*, 201, 1061-1067.

Marie, J. C., Liggitt, D. and Rudensky, A. Y. (2006) Cellular mechanisms of fatal early-onset autoimmunity in mice with the T cell-specific targeting of transforming growth factor-beta receptor.[see comment]. *Immunity*, 25, 441-454.

Nikolcheva, T., Pyronnet, S., Chou, S. Y., Sonenberg, N., Song, A., Clayberger, C. and Krensky, A. M. (2002) A translational rheostat for RFLAT-1 regulates RANTES expression in T lymphocytes. *Journal of Clinical Investigation*, 110, 119-126.

Noti, J. D., Johnson, A. K. and Dillon, J. D. (2004) The zinc finger transcription factor transforming growth factor beta-inducible early gene-1 confers myeloid-specific activation of the leukocyte integrin CD11d promoter. *Journal of Biological Chemistry*, 279, 26948-26958.

Nuez, B., Michalovich, D., Bygrave, A., Ploemacher, R. and Grosveld, F. (1995) Defective haematopoiesis in fetal liver resulting from inactivation of the EKLF gene. *Nature*, 375, 316-318.

Perkins, A. C., Sharpe, A. H. and Orkin, S. H. (1995) Lethal beta-thalassaemia in mice lacking the erythroid CACCC-transcription factor EKLF. *Nature*, 375, 318-322.

Piccirillo, C. A. and Shevach, E. M. (2004) Naturally-occurring CD4+CD25+ immunoregulatory T cells: central players in the arena of peripheral tolerance. *Seminars in Immunology*, 16, 81-88.

Ribeiro, A., Bronk, S. F., Roberts, P. J., Urrutia, R. and Gores, G. J. (1999) The transforming growth factor beta(1)-inducible transcription factor TIEG1, mediates apoptosis through oxidative stress. *Hepatology*, 30, 1490-1497.

Sakaguchi, S. (2005) Naturally arising Foxp3-expressing CD25+CD4+ regulatory T cells in immunological tolerance to self and non-self. *Nature Immunology*, 6, 345-352.

Shi, C., Feinberg, M. W., Zhang, D., Patel, A., Sim, C. U., Dong, Z. M., Chapman, S. M., Gutierrez-Ramos, J. C., Wagner, D. D., Sibinga, N. E. and Haber, E. (1999) Donor MHC and adhesion molecules in transplant arteriosclerosis. *Journal of Clinical Investigation*, 103, 469-474.

Shi, Y. and Massague, J. (2003) Mechanisms of TGF-beta signaling from cell membrane to the nucleus. *Cell*, 113, 685-700.

Shull, M. M., Ormsby, I., Kier, A. B., Pawlowski, S., Diebold, R. J., Yin, M., Allen, R., Sidman, C., Proetzel, G. and Calvin, D. (1992) Targeted disruption of the mouse transforming growth factor-beta 1 gene results in multifocal inflammatory disease. *Nature*, 359, 693-699.

Song, A., Chen, Y. F., Thamatrakoln, K., Storm, T. A. and Krensky, A. M. (1999) RFLAT-1: a new zinc finger transcription factor that activates RANTES gene expression in T lymphocytes. *Immunity*, 10, 93-103.

Subramaniam, M., Gorny, G., Johnsen, S. A., Monroe, D. G., Evans, G. L., Fraser, D. G., Rickard, D. J., Rasmussen, K., van Deursen, J. M., Turner, R. T., Oursler, M. J. and Spelsberg, T. C. (2005) TIEG1 null mouse-derived osteoblasts are defective in mineralization and in support of osteoclast differentiation in vitro. *Molecular & Cellular Biology*, 25, 1191-1199.

Subramaniam, M., Harris, S. A., Oursler, M. J., Rasmussen, K., Riggs, B. L. and Spelsberg, T. C. (1995) Identification of a novel TGF-beta-regulated gene encoding a putative zinc finger protein in human osteoblasts. *Nucleic Acids Research*, 23, 4907-4912.

Tachibana, I., Imoto, M., Adjei, P. N., Gores, G. J., Subramaniam, M., Spelsberg, T. C. and Urrutia, R. (1997) Overexpression of the TGFbeta-regulated zinc finger encoding gene, TIEG, induces apoptosis in pancreatic epithelial cells. *Journal of Clinical Investigation*, 99, 2365-2374.

Tang, Q. and Bluestone, J. A. (2008) The Foxp3+ regulatory T cell: a jack of all trades, master of regulation. *Nature Immunology*, 9, 239-244.

Venuprasad, K., Huang, H., Harada, Y., Elly, C., Subramaniam, M., Spelsberg, T., Su, J. and Liu, Y. C. (2008) The E3 ubiquitin ligase Itch regulates expression of transcription factor Foxp3 and airway inflammation by enhancing the function of transcription factor TIEG1. *Nature Immunology*, 9, 245-253.

von Boehmer, H. (2005) Mechanisms of suppression by suppressor T cells. *Nature Immunology*, 6, 338-344.

Wan, Y. Y. and Flavell, R. A. (2005) Identifying Foxp3-expressing suppressor T cells with a bicistronic reporter. *Proceedings of the National Academy of Sciences of the United States of America*, 102, 5126-5131.

Warke, V. G., Nambiar, M. P., Krishnan, S., Tenbrock, K., Geller, D. A., Koritschoner, N. P., Atkins, J. L., Farber, D. L. and Tsokos, G. C. (2003) Transcriptional activation of the human inducible nitric-oxide synthase promoter by Kruppel-like factor 6. *J Biol Chem*, 278, 14812-14819.

Yang, X. O., Doty, R. T., Hicks, J. S. and Willerford, D. M. (2003) Regulation of T-cell receptor D beta 1 promoter by KLF5 through reiterated GC-rich motifs. *Blood*, 101, 4492-4499.

Zheng, S. G., Wang, J. H., Gray, J. D., Soucier, H. and Horwitz, D. A. (2004) Natural and induced CD4+CD25+ cells educate CD4+CD25- cells to develop suppressive activity: the role of IL-2, TGF-beta, and IL-10. *Journal of Immunology*, 172, 5213-5221.

Zheng, Y. and Rudensky, A. Y. (2007) Foxp3 in control of the regulatory T cell lineage. *Nature Immunology*, 8, 457-462.

Zhou, M., McPherson, L., Feng, D., Song, A., Dong, C., Lyu, S. C., Zhou, L., Shi, X., Ahn, Y. T., Wang, D., Clayberger, C. and Krensky, A. M. (2007) Kruppel-like transcription factor 13 regulates T lymphocyte survival in vivo. *Journal of Immunology*, 178, 5496-5504.

Zhou, X., Nicoletti, A., Elhage, R. and Hansson, G. K. (2000) Transfer of CD4(+) T cells aggravates atherosclerosis in immunodeficient apolipoprotein E knockout mice.[see comment]. *Circulation*, 102, 2919-2922.

Zhou, X., Robertson, A. K., Hjerpe, C. and Hansson, G. K. (2006) Adoptive transfer of CD4+ T cells reactive to modified low-density lipoprotein aggravates atherosclerosis. *Arteriosclerosis, Thrombosis & Vascular Biology*, 26, 864-870.

Ziegler, S. F. (2006) FOXP3: of mice and men. *Annual Review of Immunology*, 24, 209-226.

EQUIVALENTS

In the foregoing specification, this invention has been described in relation to certain embodiments thereof, and many details have been set forth for purposes of illustration. Nevertheless, it will be apparent to those skilled in the art that the invention is susceptible to additional embodiments and that certain of the details herein may be varied considerably without departing from the basic principles of the invention. Likewise, those skilled in the art will recognize, or be able to ascertain using no more than routine experimentation, many equivalents of the specific embodiments of the invention described herein. Such equivalents are intended to be encompassed by the following claims.

The invention claimed is:

1. A method for identifying a candidate compound that induces a T regulatory phenotype in CD4+/CD25− cells, comprising the steps of:
   contacting a CD4+/CD25− cell comprising a reporter gene under the control of a KLF10 promoter with a candidate compound;
   detecting the expression level of the reporter gene,
   wherein upregulation of the reporter gene is indicative of a compound that induces the T regulatory phenotype.

* * * * *